US006429017B1

(12) United States Patent
Toh et al.

(10) Patent No.: US 6,429,017 B1
(45) Date of Patent: Aug. 6, 2002

(54) METHOD FOR PREDICTING THE PRESENCE OF HAEMOSTATIC DYSFUNCTION IN A PATIENT SAMPLE

(75) Inventors: Cheng Hock Toh; Colin Downey, both of Liverpool (GB); Timothy J. Fischer, Raleigh, NC (US)

(73) Assignee: bioMerieux, Durham, NC (US)

( * ) Notice: Subject to any disclaimer, the term of this patent is extended or adjusted under 35 U.S.C. 154(b) by 0 days.

(21) Appl. No.: 09/372,954

(22) Filed: Aug. 12, 1999

Related U.S. Application Data

(63) Continuation-in-part of application No. 09/244,340, filed on Feb. 4, 1999.

(51) Int. Cl.$^7$ .............................................. G01N 33/86
(52) U.S. Cl. ............................. 436/69; 436/73; 436/74; 436/79; 436/84; 436/164; 422/73; 422/82.09; 600/369; 73/64.41; 73/64.43
(58) Field of Search ............................. 436/63, 69, 73, 436/74, 79, 84, 164; 422/68.1, 73, 82.09; 600/369; 73/64.41, 64.43

(56) References Cited

U.S. PATENT DOCUMENTS

| | | | |
|---|---|---|---|
| 3,307,392 A | 3/1967 | Owen et al. ................. 73/64.1 |
| 3,458,287 A | 7/1969 | Gross et al. .................. 23/230 |
| 3,658,480 A | 4/1972 | Kane et al. ................ 23/230 B |
| 4,040,788 A | * 8/1977 | Simons et al. |
| 4,047,890 A | 9/1977 | Eichelberger et al. .... 23/230 B |
| 4,199,748 A | 4/1980 | Bacus ............... 340/146.3 CA |
| 4,217,107 A | 8/1980 | Saito et al. ............... 23/230 B |
| 4,279,616 A | 7/1981 | Saito et al. ............... 23/230 B |
| 4,289,498 A | 9/1981 | Baughman et al. ....... 23/230 B |
| 4,766,083 A | 8/1988 | Miyashita et al. .......... 436/517 |

(List continued on next page.)

FOREIGN PATENT DOCUMENTS

| | | | |
|---|---|---|---|
| DE | 2635081 | 2/1978 | .......... G01N/33/16 |
| DE | 3502 878 | 1/1985 | ........... C12Q/01/56 |
| EP | 0 115 459 | 8/1984 | .......... G01N/33/68 |
| EP | 0 434 377 | 6/1991 | .......... G01N/33/86 |
| EP | 0 525 273 | 2/1993 | .......... G01N/33/49 |
| EP | 818680 | 1/1998 | |
| EP | 841 566 | 5/1998 | .......... G01N/33/96 |
| FR | 2364 453 | 9/1976 | .......... G01N/33/16 |
| GB | 2005014 | 4/1979 | .......... G01N/33/16 |
| JP | 59-203959 | 11/1984 | .......... G01N/33/86 |

(List continued on next page.)

OTHER PUBLICATIONS

International Search Report, International Application No. PCT/US00/21022, Dated Jan. 22, 2001.

McCarty et al., "Historical Perspective on C–Reactive Protein," Laboratory of Bacteriology and Immunology, vol. 389, 1982, pp. 1–10.

Simmons A., "Technical Hematology (Third Edition)," National Health Laboratories, Plainview, NY, pp. 334–5.

Rowe et al., "Circulating Human C–Reactive Protein Binds Very Low Density Lipoproteins," Clin. Exp. Immunol., 1984, No. 58, pp. 237–244.

Rowe et al., "Rabbit and Rat C–Reactive Proteins Bind Apolipoprotein B–Containing Lipoproteins," J. Exp. Med., 1984, vol. 159, pp. 604–16.

Gewurz et al., "C–Reactive Protein and the Acute Phase Response," Advances in Internal Medicine, 1982, 27: pp. 345–372.

Sammalkorpi et al., "Lipoproteins and Acute Phase Response During Acute Infection. Interrelationships Between C–Reactive Protein and Serum Amyloid–A Protein and Lipoproteins," Annals of Medicine, 1990, 22: pp. 397–401.

Stewart et al., "Sensitive and Rapid Measurement of C–Reactive Protein (CRP) by Lipid Agglutination," Dept. of Laboratory Medicine, Nov. 1986, pp. 585–8.

Hulman et al., "Comparison of Fat Agglutination Slide Test and Latex for C–Reactive Protein," Clinica Chimica Acta, 165, (1987), pp. 89–93.

Lagrand et al., "C–Reactive Protein as a Cardiovascular Risk Factor More Than an Epiphenomenon?," Circulation Jul. 1999, pp. 96–102.

Hulman, G., "The Pathogenesis of Fat Embolism," Journal of Pathology, 1995, vol. 176: pp. 3–9.

Lindh et al., "Agglutinate Formation in Serum Samples Mixed With Intravenous fat Emulsions," Critical Care Medicine, vol. 13, No. 3, 1985, pp. 151–3.

Husebekk et al., "High–Density Lipoprotein has Different Binding Capacity for Different Apoproteins the Amyloidogenic Apoproteins are Easier to Displace from High–Density Lipoprotein," Scan. J. Immunol., 28, (1988), pp. 653–658 (abstract only).

Husebekk et al., "High–Density Lipoprotein has Different Binding Capacity for Different Apoproteins the Amyloidogenic Apoproteins are Easier to Displace from High––Density Lipoprotein," Scan. J. Immunol., 28, (1988), pp. 653–658 (abstract only).

Eitoku et al., "Studies on the Serum Amyloid A (SAA): Part 2 Latex Agglutination Nephelometric Immunoassay System for the Quantitation of SAA in Human Serum and its Clinical Values," Physico Chem. Biol., vol. 37, (1993), No. 1, pp. 19–23 (abstract only).

(List continued on next page.)

Primary Examiner—Maureen M. Wallenhorst
(74) Attorney, Agent, or Firm—Myers Bigel Sibley & Sajovec

(57) ABSTRACT

A method which may be used to determine haemostatic dysfunction in a patient is carried out by (a) adding a reagent to a test sample, wherein the test sample includes at least a component of a blood sample from a patient; and then (b) measuring the formation of a precipitate due to the reaction of the test sample and the reagent, over time so as to derive a time-dependent measurement profile, the reagent forming a precipitate in the test sample without causing substantial fibrin polymerization.

35 Claims, 28 Drawing Sheets

U.S. PATENT DOCUMENTS

| | | | |
|---|---|---|---|
| 4,782,014 A | 11/1988 | Serban et al. | 435/7.95 |
| 4,902,630 A | 2/1990 | Bennett et al. | 436/546 |
| 4,965,725 A | 10/1990 | Rutenberg | 364/413.1 |
| 4,998,535 A | 3/1991 | Selker et al. | 128/696 |
| 5,003,065 A | 3/1991 | Merritt et al. | 540/469 |
| 5,055,412 A * | 10/1991 | Proksch | 436/69 |
| 5,156,974 A | 10/1992 | Grossman et al. | 436/69 |
| 5,169,786 A | 12/1992 | Carroll et al. | 436/69 |
| 5,218,529 A | 6/1993 | Meyer et al. | 364/413.01 |
| 5,221,628 A | 6/1993 | Anderson et al. | 436/507 |
| 5,358,852 A | 10/1994 | Wu | 435/7.94 |
| 5,388,164 A | 2/1995 | Yonekawa et al. | 382/6 |
| 5,473,551 A | 12/1995 | Sato et al. | 364/496 |
| 5,473,732 A | 12/1995 | Chang | 395/77 |
| 5,500,345 A | 3/1996 | Soe et al. | 435/7.1 |
| 5,525,477 A | 6/1996 | Hassouna | 436/69 |
| 5,526,111 A | 6/1996 | Collins et al. | 73/64.43 |
| 5,553,616 A | 9/1996 | Ham et al. | 128/633 |
| 5,563,983 A | 10/1996 | Nozaki et al. | 395/23 |
| 5,567,596 A | 10/1996 | Diamond et al. | 435/13 |
| 5,591,403 A | 1/1997 | Gavin et al. | 422/73 |
| 5,593,897 A | 1/1997 | Potempa et al. | 436/507 |
| 5,646,046 A * | 7/1997 | Fischer et al. | 436/49 |
| 5,670,329 A | 9/1997 | Oberhardt | 435/13 |
| 5,705,395 A | 1/1998 | Griffin et al. | 436/69 |
| 5,708,591 A * | 1/1998 | Givens et al. | 364/497 |
| 5,715,821 A | 2/1998 | Faupel | 1286/653.1 |
| 5,716,795 A | 2/1998 | Matschiner | 435/13 |
| 5,834,223 A | 11/1998 | Griffin et al. | 435/13 |
| 5,856,114 A | 1/1999 | Mann et al. | 436/13 |
| 5,862,304 A | 1/1999 | Ravdin et al. | 395/22 |
| 5,981,285 A | 11/1999 | Carroll et al. | 702/23 |
| 6,010,911 A | 1/2000 | Baugh et al. | 422/73 |
| 6,040,147 A | 3/2000 | Ridker et al. | 435/7.24 |
| 6,101,449 A * | 8/2000 | Givens et al. | 702/22 |
| 6,269,313 B1 | 7/2001 | Givens et al. | 702/22 |

FOREIGN PATENT DOCUMENTS

| | | | | |
|---|---|---|---|---|
| JP | 60-114768 | 6/1985 | | G01N/35/02 |
| JP | 61-272655 | 12/1986 | | G01N/33/49 |
| JP | 05-180835 | 12/1991 | | G01N/33/53 |
| JP | 06-027115 | 7/1992 | | G01N/33/86 |
| JP | 04/254760 | 9/1992 | | |
| JP | 06-249855 | 9/1994 | | G01N/33/86 |
| JP | 10-104239 | 9/1996 | | G01N/33/86 |
| RU | 2012877 | 4/1991 | | G01N/33/48 |
| RU | 2061953 | 6/1996 | | G01N/33/86 |
| RU | 2070327 | 12/1996 | | G01N/33/50 |
| SU | 590665 | 2/1976 | | G01N/33/16 |
| SU | 1076086 | 2/1984 | | A61B/5/14 |
| SU | 1691741 | 8/1989 | | G01N/33/48 |
| SU | 1777089 | 6/1990 | | G01N/33/86 |
| WO | WO 86/06840 | 11/1986 | | G01N/33/86 |
| WO | WO 8909628 | 10/1989 | | |
| WO | WO 9100872 | 1/1991 | | |
| WO | WO 91/01383 | 2/1991 | | C12Q/1/56 |
| WO | WO 91/01497 | 2/1991 | | G01N/31/00 |
| WO | WO 91/02812 | 3/1991 | | C12Q/1/56 |
| WO | WO 9105874 | 5/1991 | | |
| WO | WO 91/08460 | 6/1991 | | G01N/21/00 |
| WO | WO 91/16453 | 10/1991 | | C12Q/1/56 |
| WO | WO 93/07491 | 4/1993 | | G01N/33/68 |
| WO | WO 9309438 | 5/1993 | | |
| WO | WO 9324530 | 12/1993 | | |
| WO | WO 94/07145 | 3/1994 | | G01N/33/86 |
| WO | WO 94/11714 | 5/1994 | | G01J/3/02 |
| WO | WO 94/16095 | 7/1994 | | C12Q/1/00 |
| WO | WO 95/05590 | 2/1995 | | G01N/1/28 |
| WO | WO 95/08121 | 3/1995 | | G01N/33/86 |
| WO | WO 96/42018 | 9/1995 | | G01N/33/86 |
| WO | WO 95/30154 | 11/1995 | | G01N/33/86 |
| WO | WO 9606624 | 3/1996 | | |
| WO | WO 96/14581 | 5/1996 | | G01N/33/86 |
| WO | WO 96/21740 | 7/1996 | | C12Q/1/56 |
| WO | WO 96/41291 | 12/1996 | | G06F/19/00 |
| WO | WO 9704317 | 2/1997 | | |
| WO | WO 97/20066 | 6/1997 | | C12Q/1/56 |
| WO | WO 97/34698 | 9/1997 | | B01L/3/00 |
| WO | WO 98/09628 | 3/1998 | | A61K/31/495 |
| WO | WO99/34208 | 7/1999 | | |
| WO | WO99/47699 | 9/1999 | | |

OTHER PUBLICATIONS

McDonald et al., "A monoclonal Antibody Sandwich Immunoassay for Serum Amyloid A (SAA) Protein," J. Immunol. Methods, 1991, 144, No. 2, pp. 149–155 (abstract only).

Wilkins et al., "Rapid Automated Enzyme Immunoassay of Serum Amyloid A," Clin. Chem, 1994, vol. 40, No. 7, Part 1, pp. 1284–1290 (abstract only).

Harris et al., "Reactivity of Serum Amyloid P Component with C–Reactive Protein and IgM," Clin. Res., 37, (1989), No. 2, 614A (abstract only).

Christner et al., "Specificity of the Binding Interaction Between Human Serum Amyloid P–component and Immobilized Human C–Reactive Protein," J. Biol. Chem., 1994, 269, No. 13, pp. 9760–6 (abstract only).

Swanson et al., "Human Serum Amyloid P–component (SAP) Selectively binds to Immobilized or Bound Forms of C–Reactive Protein (CRP)," Biochem. Biophys. Acta, 1992, 1160, No. 3, pp. 309–316 (abstract only).

Robin et al., "Prognostic Value of Waveform Analysis in the Intensive Care Setting," Intensive Care Med., 1999:25 (Supplement 1): S63.

Toh et al., "A Previously Unrecognised Mechanism that is Calcium–dependent and Thrombin–independent Characterises the Pre–DIC State," The American Society of Hematology, 1999 Submission Form (Draft Preview of Abstract #450426).

Toh et al., "Prospective Detection of Pre–Disseminated Intravascular Coagulation (DIC) in a Sepsis Cohort by Waveform Analysis," XVIIth Congress International Society for Thrombosis & Haemostasis, Aug. 1999 (abstract submission form).

Toh et al., "APTT Waveform Analysis: Predicting Mortality in the Critical Care Setting Using the Light Transmittance Level at 18 Seconds," XVIIth Congress International Society for Thrombosis & Haemostasis, Aug. 1999 (abstract submission form).

Toh et al., "Waveform Analysis of the Prothrombin Time (PT) Assay also Shows Characteristic Changes in Disseminated Intravascular Coagulation," XVIIth Congress International Society for Thrombosis & Haemostasis, Aug. 1999 (abstract submission form).

Downey et al., "The Robustness and Reproducibility of APIT Waveform Analysis in Relation to Reagent and Batch Variation," (abstract only).

Dennis et al., "Utility of Prothrombin Time Waveform Analysis in the Routine Clinical Setting," Sep. 1999 (abstract submission form).

Toh et al., "Impending Clinical Decompensation is Characterised by the Detection of a Novel Calcium–dependent and Thrombin–independent Pathway," 5th World Congress on Trauma, Shock, Inflammation and Sepsis—Pathophysiology, Immune Consequences and Therapy, Feb. 2000 (abstract submission form).

Toh et al., "Characterisation of the Novel Calcium–Activation, Thrombin Suppression Assay (CaTs) in the DIC of Sepsis," abstract only).

Toh et al., "The Mechanism Underlying the Atypical Clot Waveform Profile of DIC is Thrombin–independent but Calcium–dependent," European Haematology Association, Jun. 2000 (abstract only).

Schwalbe et al., "Association of Rat C–Reactive Protein and Other Pentraxins with Rat Lipoproteins Containing Apolipoproteins E and A1," Biochemistry, 1995, 34 (33), 10432–9.

Toh et al., "Disseminated Intravascular Coagulation (DIC): Old Problem, New Hope," Clinical Hemostasis Review, Jan. 1998.

Downey et al., "Novel and Diagnostically Applicable Information from Optical Waveform Analysis of Blood Coagulation In Disseminated Intravascular Coagulation," British Journal of Haematology, 1997.97.000–000.

Downey et al., "Transmittance Waveforms–Adjunctive Information from Automated Coagulometers,"International Journal of Hematology, Abstracts of the 26th Congress of the International Society of Haematology 25–29, Aug. 1996 (abstract only).

Engler, R., "Acute–phse Proteins in Inflammtion," CR Seances Soc. Biol. Fil., 1995, vol. 189 (4), pp. 563–78 (abstract only).

Rybarska et al., "The Detection of Specific Acute Phase Serum Protein Complexes and Immune Complexes by Congo Red Binding," Journal Physiology and Pharmacology, 1995, vol. 46(2), pp. 221–31 (abstract only).

Maury, C.P.J., "Clinical Usefulness of Serum amyloid A and C–reactive Protein Measurements in Inflammatory Disorders a Comparative Study," Marker Proteins in Inflammation Proceedings, vol. 3, Symposium, Lyon, France, Jun. 1985 (abstract only).

Richter et al., "The Fat Emulsion Agglutination Test: A Reliable and Cost Effective Alternative to the Latex Agglutination Test for Rapid Bedside CRP Measurement," Clinica Chimica Acta, 261, 1997, pp. 141–148.

Rowe et al., "Agglutination of Intravenous Lipid Emulsion ('Intralipid') and Plasma Lipoproteins by C–reactive Protein," Clin. Exp. Immunol., 1986, No. 66, pp. 241–7.

Hulman et al., "Agglutination of Intralipid by Sera of Actuely III Patients," The Lancet, Dec. 1982, p. 1426.

Cabana et al., "Interaction of Very Low Density Lipoproteins (VLDL) with Rabbit C–reactive Protein," J Immunol, 1982, vol. 128 (5), pp. 2342–8 (abstract only).

Cabana et al., "Inflammation–induced Changes in Rabbit CRP and Plsma Lipoproteins," J Immunol, 1983, vol. 130(4), pp. 1736–42 (abstract only).

Cabana et al., "Effects of the Acute Phase Response on the Concentration and Density Distribution of Plasma Lipids and Apolipoproteins," J Lipid Res.1989, vol. 30(1), pp. 39–49 (abstract only).

de Beer et al., "Low Density Lipoprotein and Very Low Density Lipoprotein are Selectively Bound by Aggregated C–reactive Protein," J Exp Med., 1982, vol. 156(1), pp. 230–42 (abstract only).

Pepys et al., "C–reactive Protein: Binding to Lipids and Lipoproteins," Int Rev Exp Pathol., 1985, vol. 27, pp. 83–111 (abstract only).

Rowe et al., "In vivo Turnover Studies of C–reactive Protein and Lipoproteins in the Rabbit," Clin Exp Immunol, vol. 58(1), pp. 245–52 (abstract only).

Cabana et al., "Effects of the Acute Phase Response on the Concentration and Density Distribution of Plasma Lipids and Apolipoproteins," Journal of Lipid Research, vol. 30, 1989, pp. 39–49.

Canivet et al., "Postoperative Changes in Lipid Profile: Their Relations with Inflammatory Markers and Endocrine Mediators," Acta Anaesthesiologica Belgica, vol. 40 (4), 1989.

Atherotech—VAP/CAD Lipoprotein Risk Assessment Test, Sample of VAP Profile.

Malle et al., "Serum Amyloid A (SAA): An Acute Phase Protein and Apolipoprotein," Atherosclerosis 1993, 102, pp. 131–146.

3 × 15 Test Kit for Detection of Plasma Protein C Activity Using a Clotting End–Point, Product # ACC–45, American Diagnostica Inc., 1–2 (Feb. 1989).

Astion, et al., Overtraining in neural networks that interpret clinical data, Clin. Chem., 39(9):1998–2004 (1993).

Astion, et al., The application of backpropagation neural networks to problems in pathology and laboratory medicine, Arch. Pathol. Lab. Med., 116:995–1001 (Oct. 1992).

Baum and Haussler, What size net gives valid generalization?, Neural Computation, pp. 81–89 (Jan. 1989).

Baumann, et al., Computerized analysis of the in vitro activation of the plasmatic clotting system, Haemostasis, 19:309–321 (1989).

Bluestein and Archer, The sensitivity, specificity and predictive value of diagnostic information: a guide for clinicians, Nurse Practitioner, 16(7):39–45 (Jul. 1991).

Boone et al., Neural networks in radiologic diagnosis, Investigative Radiology, 25(9):1013–1023 (Sep. 1990).

Brandt, et al., Effect of lupus anticoagulants on the activated partial thromboplastin time. Results of the College of American Pathologists survey program, Arch.Pathol.Lab Med., 115:109–114 (Feb. 1991).

Braun et al., Examination of prothrombin time (PT) and activated partial thromboplastin time (APTT) optical clot profiles using an automated thromobosis–hemostasis, Coagulation Methods Instrumentation and Quality Control, p. 1236, Abstract #1286 (1995).

Braun, et al., Properties of optical data from activated partial thromboplastin time and prothrombin time assays, Thromb. Haemost., 78:1079–1987 (1997).

Carrol, et al., Ortho Educational Monograph, The Clot Signature and New Aspects in Coagulation Testing, Ortho Diagnostic Systems, Inc., pp. 1–20 (1989).

Dassen, et al., Self–learning neural networks in electrocardiography, J. Electrocardiol., 23 Suppl:200–202 (1990).

Furlong, et al., Neural network analysis of serial cardiac enzyme data. A clinical application of artificial machine intelligence, Am.J.Clin.Pathol., 96(1):134–141 (Jul. 1991).

Givens and Braun, Classification of factor deficiencies from coagulation assays using neural networks, Int.J.Med.Inf., 46:129–143 (1997).

Givens et al., Interpretation of clot formation parameters from APTT and PT assays using neural networks, Clin.Chem., 42(6):S192, Abstract #399 (1996).

Givens, et al., Predicting the presence of plasma heparin using neural networks to analyze coagulation screening assay optical profiles, *Comput.Biol.Med.*, 26(6):463–476 (1996).

Givens, T.B., Clot signatures, *Clin.Hemostasis Rev.*, pp. 11–12 (Aug. 1997).

Heuck and Baumann, Kinetic analysis of the clotting system in the presence of heparin and depolymerized heparin *Haemostasis*, 21:10–18 (1991).

Hoffman and Callahan, The Coag–A–Mate RA4 Fibrinogen Assay, *Interface* (Organon Teknika), pp. 3–7 (1990).

*Koagulab 16–S Plus Graphics, Koagulab 32–S Coagulation System, Graphics Binder*, 2,3,5,6,8–12, 14–17, 19–21, 23.

Khanin and Semenov, A mathematical model of the kinetics of blood coagulation, *J. Theor.Biol.*, 136:127–134 (Jan. 1989).

Package insert for Ortho Brain Thromboplastic Reagent, *Ortho Diagnostic System, Inc.*, pp. 1–7 (Oct. 1985).

Pattichis, et al., Efficient training of neural network models in classification of electromyographic data, *Med.Biol.Eng Comput.*, 33(3):499–503 (May 1995).

Pohl, et al., The quick machine–a mathematical model for the extrinsic activation of coagulation, *Haemostasis*, 24:325–337 (1994).

Sabbatini, R.M.E., Neural networks for classification and pattern recognition of biological samples, *Conf.of the Engineering in Medicine and Biology Society* (IEEE, New York, U.S.) 15:265–266 (Oct. 1983).

Schweiger, et al., Evaluation of laboratory data by conventional statistics and by three types of neural networks, *Clin.Chem.*, 39(9):1966–1971 (1993).

Sweeney et al., Abnormal clot signatures in hereditary bleeding disorders, *Blood*, 74 Suppl 1(7):395, Abstract #1509 (Nov. 1989).

Sweeney et al., Abnormal clot signatures in hereditary bleeding disorders, *The American Society of Hematology Abstract Reproduction Form* (1989).

Sweeney et al., Kinetic clot parameters in gynecological tumors, *Blood*, 76 Suppl 1(10):439a, Abstract #1745–(Nov. 1990).

Swets, J. A., Measuring the accuracy of diagnostic systems, *Science*, 240:1285–1293 (Jun. 1988).

Talstad, I., Which coagulation factors interfere with the one–stage prothrombin time?, *Haemostasis*, 23:19–25 (1993).

Triplett, et al., Graphic monitoring of coagulation assays, *American Clinical Laboratory*, pp. 1–5 (Apr. 1989).

Zweig and Campbell, Receiver–operating characteristic (ROC) plots: a fundamental evaluation tool in clinical medicine, *Clin.Chem.*, 39(4):561–577 (1993).

*Ortho Factor VIII: C Deficient Plasma*, Ortho Diagnostic Systems, Inc., pp. 1–2 (Sep. 1998).

C. Downey, et al. *Br. J. Haematol.*, 136: 18854 (1997).

Baumann et al., "Simulation of the extrinsic pathway of the plasmatic clotting system," *Haemostasis*, 21:329–337 (1991).

Zuckerman et al. "Comparison of thrombelastography with common coagulation tests," *Thromb Haemostas*, 46: 752–756 (1981).

\* cited by examiner

Plasms CRP Levels and Calcium−Induced Thurbidity Changes.

| Plasma Sample | [CRP], ug/ml | delta A405nm |
|---|---|---|
| Normal Human Pool | 0.73 | 0 |
| Pt#1 | 248 | 0.329 |
| Pt#2 | 277 | 0.235 |
| Pt#3 | 319 | 0.345 |
| Pt#4 | 443 | 0.170 |
| Pt#5 | 478 | 0.640 |
| Pt#6 | 492 | 0.230 |
| Pt#7 | 528 | 0.140 |
| Pt#8 | 576 | 0.640 |
| Pt#9 | 600 | 0.390 |
| Pt#10 | 639 | 0.160 |

FIG. 24

METHOD FOR PREDICTING THE PRESENCE OF HAEMOSTATIC DYSFUNCTION IN A PATIENT SAMPLE

This application is a continuation-in-part of U.S. patent application Ser. No. 09/244,340, filed Feb. 4, 1999, the subject matter of which is incorporated herein by reference. This application also relates to U.S. Pat. No. 5,646,046 to Fischer et al., the subject matter of which is incorporated herein by reference.

BACKGROUND OF THE INVENTION

Blood clots are the end product of a complex chain reaction where proteins form an enzyme cascade acting as a biologic amplification system. This system enables relatively few molecules of initiator products to induce sequential activation of a series of inactive proteins, known as factors, culminating in the production of the fibrin clot. Mathematical models of the kinetics of the cascade's pathways have been previously proposed.

Thrombosis and hemostasis testing is the in vitro study of the ability of blood to form clots and to break clots in vivo. Coagulation (hemostasis) assays began as manual methods where clot formation was observed in a test tube either by tilting the tube or removing fibrin strands by a wire loop. The goal was to determine if a patient's blood sample would clot after certain materials were added. It was later determined that the amount of time from initiation of the reaction to the point of clot formation in vitro is related to congenital disorders, acquired disorders, and therapeutic monitoring. In order to remove the inherent variability associated with the subjective endpoint determinations of manual techniques, instrumentation has been developed to measure clot time, based on (1) electromechanical properties, (2) clot elasticity, (3) light scattering, (4) fibrin adhesion, and (5) impedance. For light scattering methods, data is gathered that represents the transmission of light through the specimen as a function of time (an optical time-dependent measurement profile).

Two assays, the PT and APTT, are widely used to screen for abnormalities in the coagulation system, although several other screening assays can be used, e.g. protein C, fibrinogen, protein S and/or thrombin time. If screening assays show an abnormal result, one or several additional tests are needed to isolate the exact source of the abnormality. The PT and APTT assays rely primarily upon measurement of time required for clot time, although some variations of the PT also use the amplitude of the change in optical signal in estimating fibrinogen concentration.

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APTT assay, which gives a prolonged clot time in the presence of heparin. Clot times for PT assays are affected to a much smaller degree. Since a number of other plasma abnormalities may also cause prolonged APTT results, the ability to discriminate between these effectors from screening assay results may be clinically significant.

The present invention was conceived of and developed for predicting haemostatic dysfunction in a sample based on one or more time-dependent measurement profiles, such as optical time-dependent measurement profiles. In addition, the present invention is directed to predicting the presence of Disseminated Intravascular Coagulation in a patient based on a time-dependent profile, such as an optical transmission profile, from an assay run on the patient's blood or plasma sample.

SUMMARY OF THE INVENTION

The present invention is directed to a method for detecting precipitate in a test sample in the absence of clot formation. The method includes providing a test sample and adding thereto a reagent, the reagent alone or in combination with additional reagents causing the formation of a precipitate. The reagent preferably comprises a metal divalent cation and optionally includes a clot inhibiting substance. The detection of the precipitate can be qualitative or quantitative, and the precipitate can be detected such as by a clotting assay, a latex agglutination or gold sol assay, an immunoassay such as an ELISA, or other suitable method that would allow for detection and/or quantitation of the precipitate. The formation of the precipitate can be detected as an endpoint value, or kinetically. This precipitate detection allows for predicting Haemostatic Dysfunction in patients. The present invention is useful for predicting Haemostatic Dysfunction that can lead to bleeding or thrombosis, or specifically to Disseminated Intravascular Coagulation (DIC).

More particularly, the present invention is directed to a method comprising adding a reagent to a test sample having at least a component of a blood sample from a patient, measuring the formation of a precipitate due to the reaction of the test sample and the reagent, over time so as to derive a time-dependent measurement profile, the reagent capable of forming a precipitate in the test sample without causing substantial fibrin polymerization. The invention is also directed to a method for determining whether or not a patient has haemostatic dysfunction, comprising obtaining a blood sample from a patient, obtaining plasma from said blood sample, adding a reagent capable of inducing the formation of a precipitate in patients with haemostatic dysfunction without causing any substantial fibrin polymerization, taking one or more measurements of a parameter of the sample wherein changes in the sample parameter are capable of correlation to precipitate formation if present, and determining that a patient has haemostatic dysfunction if precipitate formation is detected.

The present invention is also directed to a method for determining in a patient sample the presence of a complex of proteins comprising at least one of a 300 kD protein, serum amyloid A and C-reactive protein, comprising obtaining a test sample from a patient, adding an alcohol, a clot inhibitor, and a metal cation, wherein a precipitate is formed which comprises a complex of proteins including at least one of a 300 kD protein, serum amyloid A and C-reactive protein.

The invention is also directed to a method comprising adding a coagulation reagent to an aliquot of a test sample from a patient, monitoring the formation of fibrin over time in said test sample by measuring a parameter of the test sample which changes over time due to addition of the coagulation reagent, determine a rate of change, if any, of said parameter in a period of time prior to formation of fibrin in said test sample, if the determined rate of change is beyond a predetermined threshold, then with a second aliquot of the patient test sample, add thereto a reagent that induces the formation of a precipitate in the absence of fibrin polymerization, measuring the formation of the precipitate over time, and determining the possibility or probability of haemostatic dysfunction based on the measurement of the precipitate.

The invention is also directed to a method for monitoring an inflammatory condition in a patient, comprising adding a reagent to a patient test sample, the reagent capable of causing precipitate formation in some patient test samples without causing fibrin polymerization, measuring a parameter of the test sample over time which is indicative of said precipitate formation, determining the slope of the changing parameter, repeating he the above steps at a later date or time, wherein an increase or decrease in the slope at the later date or time is indicative of progression or regression, respectively, of the inflammatory condition.

The invention is further directed to a method for diagnosing and treating patients with haemostaic dysfunction, comprising adding a reagent to a test sample that causes precipitate formation without causing fibrin polymerization, taking measurements over time of a parameter of the test sample that changes due to the formation of the precipitate, determining the rate of change of said parameter, determining that a patient has haemostatic dysfunction if said rate of change is beyond a predetermined limit; intervening with treatment for said haemostatic dysfunction if said rate of change is beyond the predetermined limit.

The invention also is directed to a method comprising adding a reagent to a patient sample capable of causing formation of a precipitate in said sample, monitoring a changing parameter of said sample over time, said parameter indicative of said precipitate formation, determining the rate of change of said parameter or whether said parameter exceeds a predetermined limit at a predetermined time, repeating the above steps at least once, each time at a different plasma/reagent ratios, measuring the maximum, average and/or standard deviation for the measurements; and determining haemostatic dysfunction based on the maximum, average and/or standard deviation measurements.

The present invention is further directed to an immunoassay comprising providing a ligand capable of binding to C-reactive protein or the 300 kD protein in lane 5 of FIG. 21, adding said ligand to a test sample from a patient and allowing binding of said ligand to C-reactive protein or said 300 kD protein in said test sample, detecting the presence and or amount of C-reactive protein or said 300 kD protein in said sample, and diagnosing haemostatic dysfunction in the patient due to the detection and/or amount of C-reactive protein or said 300 kD protein detected.

The invention further relates to a method for testing the efficacy of a new drug on a human or animal subject with an inflammatory condition and/or haemostatic dysfunction, comprising adding a reagent to a patient test sample, said reagent capable of causing precipitate formation in some subject test samples without causing fibrin polymerization, measuring a parameter of said test sample over time which is indicative of said precipitate formation, determining the slope of said changing parameter and/or the value of said parameter at a predetermined time, administering a drug to said animal or human subject, repeating the above steps at a later date or time, wherein an increase or decrease in said slope or value at said later date or time is indicative of the efficacy of said drug.

BRIEF DESCRIPTION OF THE DRAWINGS

FIGS. 21a and 21b show the non-reduced and reduced SDS page of various fractions of patient plasma;

FIG. 24 is a table showing CRP determined by ELISA;

DESCRIPTION OF THE PREFERRED EMBODIMENTS

In the present invention, not only can a particular abnormality (Haemostatic Dysfunction) be detected, but in addition the progression of the disease can be monitored in a single patient. Haemostatic Dysfunction, as used herein, is a condition evidenced by the formation of a precipitate prior to (or in the absence of clot formation, depending upon the reagent used).

Disseminated intravascular coagulation (DIC—a type of Haemostatic Dysfunction) prognosis has been hampered by the lack of an early, useful and rapidly available diagnostic marker. The invention has been found to be not only useful as an early diagnostic and single monitoring marker of DIC, but in addition the quantifiable and standardizable changes also allow for prognostic applicability in clinical management.

Disseminated intravascular coagulation (DIC) is a secondary response to a pre-existing pathology whereby the haemostatic response becomes perturbed and disseminated as opposed to the focused events of normal haemostasis. Despite improvements both in the intensive care management of patients and in our basic knowledge of haemostatic mechanisms in DIC, survival in this patient group is still very discouraging. Fundamental to the management of this complication is the implementation of aggressive therapy directed at forestalling or eradicating the primary pathology as the source of the initiating stimulus. However, in practical terms, the problem remains one of early identification of DIC to facilitate immediate and appropriate intervention. Although the technological armory available to the clinical investigator has expanded enormously, the pace of acute DIC precludes most of the more specific tests and reliance is still placed on traditional screening tests such as the prothrombin (PT), activated partial thromboplastin time (APTT) and platelet count. These tests lack specificity on an individual basis and are only useful in DIC if they lead on to further determinations of fibrinogen and fibrin breakdown products/D-dimers. However, changes in these parameters may not occur all at the same time and as such, serial testing is often needed which inevitably leads to a delay in diagnosis and clinically useful intervention.

Figure 1A:
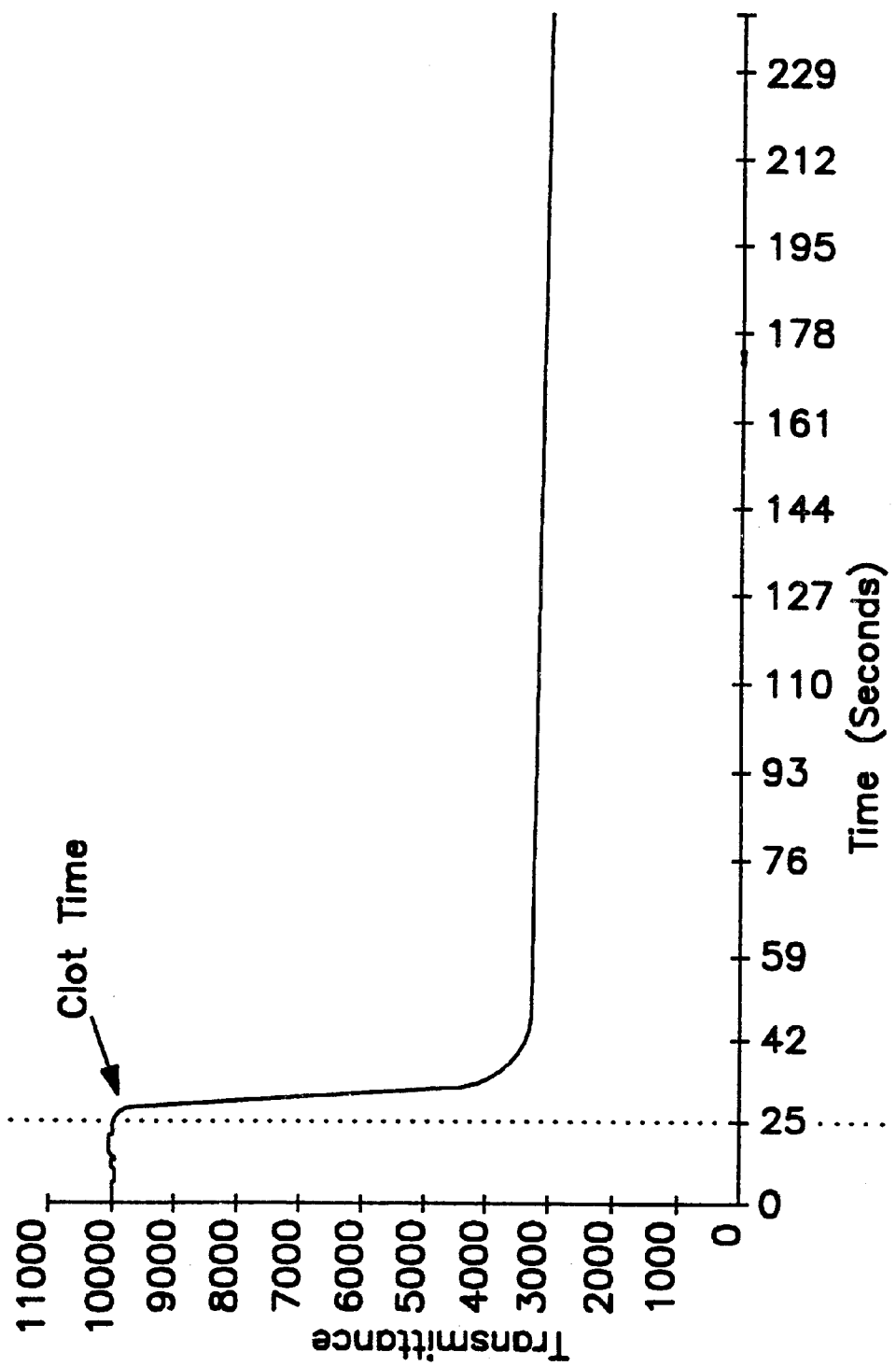
FIGS. 1a and 1b illustrate transmittance waveforms on the PTT assay with FIG. 1a showing a normal appearance, and 1b showing bi-phasic appearance.

The normal sigmoidal appearance from an APTT transmittance waveform (TW) changes to a "bi-phasic" appearance in DIC patients. This represents a loss in the plateau of a normal APTT-TW, with development of an initial low gradient slope followed by a much steeper slope (FIGS. 1a and b). In addition, this bi-phasic pattern can be seen even when the APTT clotting time result is normal.

Figure 1B:
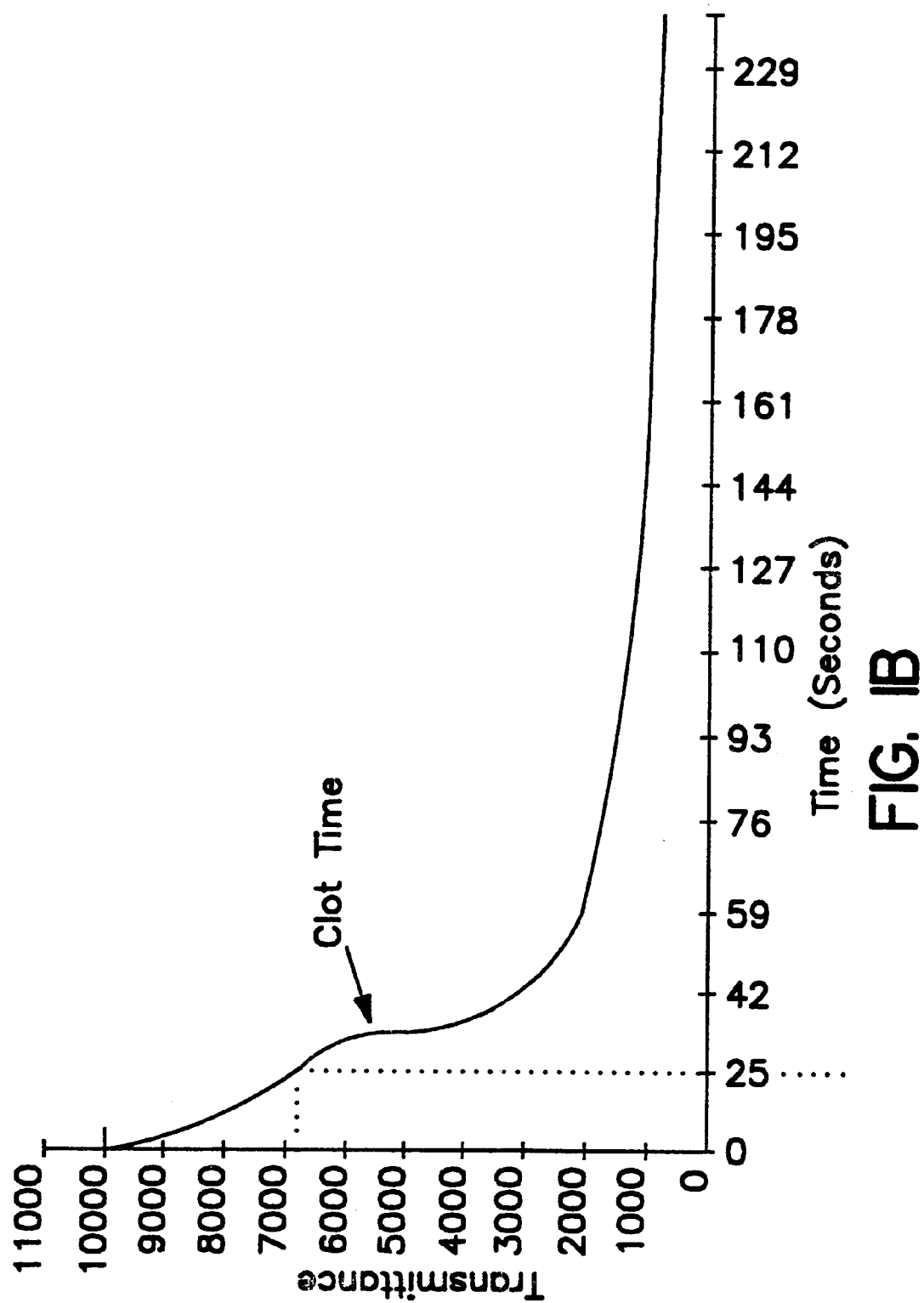

Freshly collected blood samples that required a PT or an APTT were analyzed prospectively over a two week working period. These were in 0.105M tri-sodium citrate in the ratio of 1 part anticoagulant to 9 parts whole blood and the platelet-poor plasma was analyzed on the MDA (Multichannel Discrete Analyzer) 180, an automated analyzer for performing clinical laboratory coagulation assays using an optical detection system (Organon Teknika Corporation, Durham, N.C., USA). In addition, to deriving the clot times for both PT (normal 11.2–15s) using MDA Simplastin LS and APTT (normal 23–35s) using MDA Platelin LS with 0.025M calcium chloride (Organon Teknika Corporation, USA), an analysis of the TW for the APTT was performed on each occasion at a wavelength of 580 nm. To quantitate the visual profile, the amount of light transmittance at 25 seconds was recorded. A normal waveform has a light transmittance of 100% that is represented on the analyzer and in FIG. 1a without the decimal point as 10000. As such, a bi-phasic change will have a reduced light transmittance of less than 10000. As can be seen in FIG. 1b, decreasing levels of light transmittance prior to clot formation correlate directly with increasing steepness of the bi-phasic slope. The recording of the light transmittance at 25 seconds also allows for standardization between patients and within the same patient with time. If the minimum level of light transmittance for each sample were to be used instead, this would be affected by variations in the clot time of the APTT and would therefore not be ideal for comparisons.

To ensure that no cases of DIC were overlooked, the following criteria was followed. If (a) an abnormal bi-phasic TW was encountered, or (b) a specific DIC screen was requested, or (c) if there was a prolongation in either the PT or APTT in the absence of obvious anticoagulant therapy, a full DIC screen was performed. This would further include the thrombin time (TT) (normal 10.5–15.5 seconds), fibrinogen (Fgn)(normal 1.5–3.8 g/l) and estimation of D-dimer levels (normal <0.5 mg/l) on the Nyocard D-Dimer (Nycomed Pharma AS, Oslo, Norway). Platelet counts (Plt) (normal 150–400 $10^9$/l) performed on an EDTA sample at the same time were recorded. In addition, clinical details were fully elucidated on any patient with a bi-phasic TW or coagulation abnormalities consistent with DIC.

The diagnosis of DIC was strictly defined in the context of both laboratory and clinical findings of at least 2 abnormalities in the screening tests (increased PT, increased APTT, reduced Fgn, increased TT or reduced Plt) plus the finding of an elevated D-dimer level (>0.5 mg/l) in association with a primary condition recognized in the pathogenesis of DIC. Serial screening tests were also available on those patients to chart progression and confirmation of the diagnosis of DIC as was direct clinical assessment and management. For statistical analysis, values for the sensitivity, specificity, positive and negative prediction of the APTT-TW for the diagnosis of DIC were calculated employing a two-by-two table. 95% confidence intervals (CI) were calculated by the exact binomial method.

A total of 1,470 samples were analyzed. These were from 747 patients. 174 samples (11.9%) from 54 patients had the bi-phasic waveform change. 22 of these 54 patients had more than 3 sequential samples available for analysis. DIC was diagnosed in 41 patients with 30 of these requiring transfusion support with fresh frozen plasma, cryoprecipitate or platelets. The underlying clinical disorders as shown in Table 1

TABLE 1

| Clinical disorders predisposing patients to DIC. | |
| --- | --- |
| Disorder | No |
| Infections | 17 |
| Trauma or recent major surgery | 16 |
| Malignancy | 2 |
| Hepatic Disease | 1 |
| Obstetric Cause | 1 |
| Miscellaneous Additional Causes* | 4 |

*Includes hypoxia, acidosis, Lithium overdosage and graft rejection 40 of the 41 patients with DIC had the bi-phasic TW. The one false negative result (DIC without a bi-phasic TW) occurred in a patient with pre-eclampsia (PET) where the single sample available for analysis showed a prolonged PT of 21.0s, APTT of 44.0s and raised D-dimers of 1.5 mg/l. 5 other patients were identified in this study with PET and none had either DIC or a bi-phasic TW. Of the 14 patients with a bi-phasic TW which did not fulfil the criteria of DIC, all had some evidence of a coagulopathy with abnormalities in one or two of the screening tests. These abnormal results fell short of the criterion for DIC as defined above. 4 of these 14 patients had chronic liver disease with prolonged PT and mild thrombocytopaenia. A further 2 patients had a trial fibrillation with isolated elevation of D-dimer levels only. The remaining 8 patients were on the ICU with multiple organ dysfunction arising from trauma or suspected infection but without the classical laboratory changes of DIC. These patient profiles were described in the ICU as consistent with the "systemic inflammatory response syndrome" (SIRS). Based on these figures, the bi-phasic TW has a 97.6% sensitivity for the diagnosis of DIC with a specificity of 98%. Use of an optical transmittance waveform was found to be helpful in detecting the biphasic waveform.

TABLE 2

Performance of the transmittance waveform (TW) analysis in patients with and without DIC

|  | Biphasic TW | Normal TW | Total |
|---|---|---|---|
| DIC positive | 40 | 1 | 41 |
| DIC negative | 14 | 682 | 706 |
| Total | 54 | 693 | 747 |

Sensitivity 97.6% (Cl 85.6–99.9%), Specificity 98.0% (Cl 96.6–98.9%), Positive predictive value 74.0% (Cl 60.1–84.6%), Negative predictive value 99.9% (Cl 99.1–99.9%)

Figure 2:
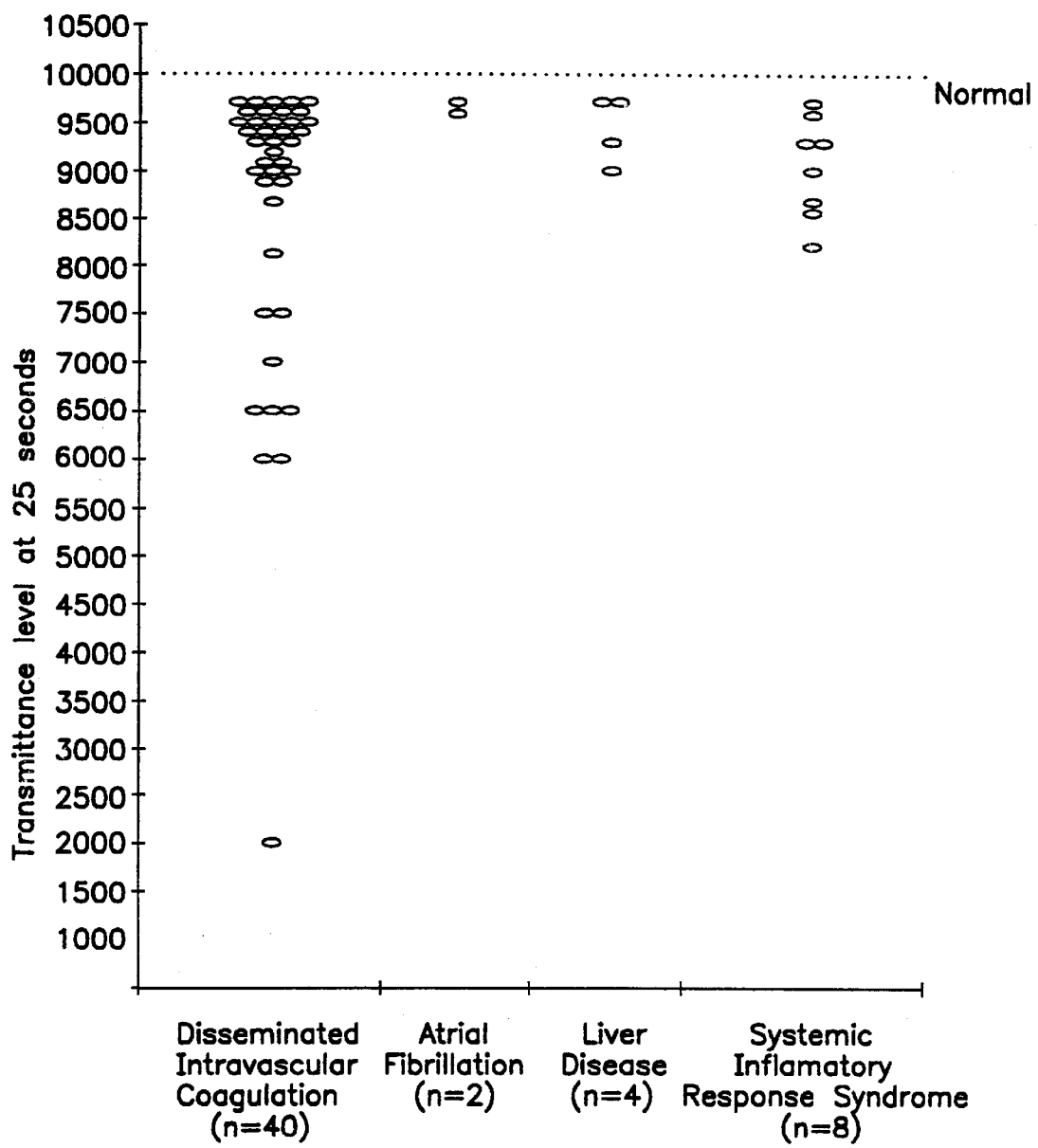
FIG. 2 illustrates transmittance levels at 25 seconds in elation to diagnosis in 54 patients with bi-phasic waveform abnormalities. The horizontal dotted line represents the normal transmittance level.
Figure 3A:
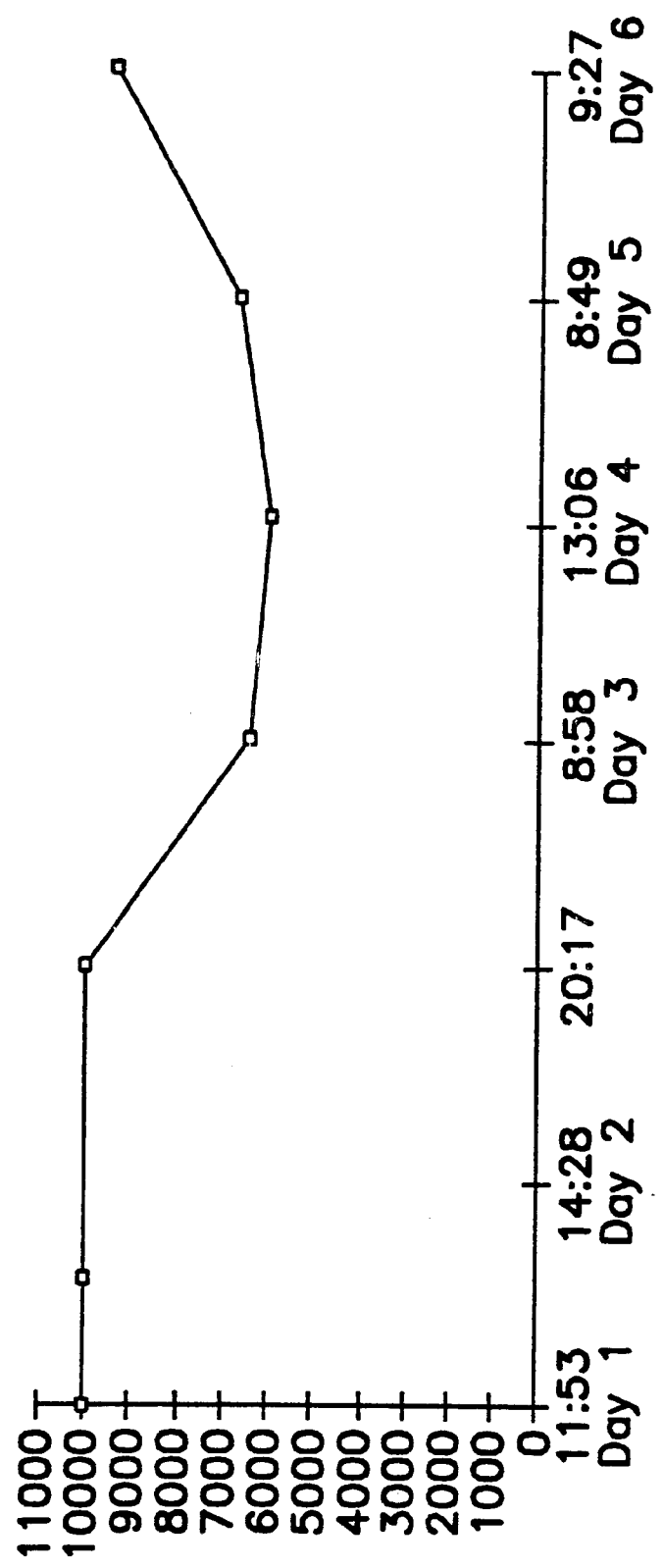
FIG. 3 illustrates serial transmittance levels (upper panel) and waveforms (lower panel) on a patient who developed DIC following sepsis and recovered.
Figure 3B:
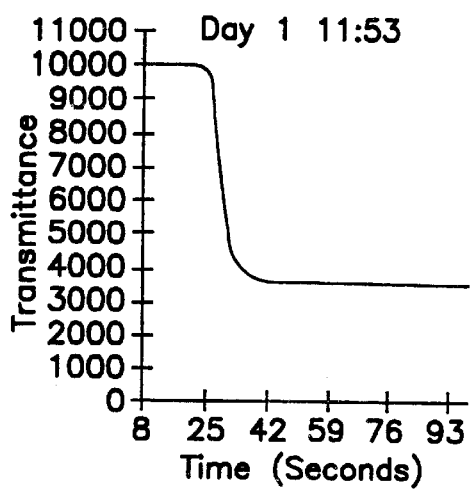
Figure 3C:
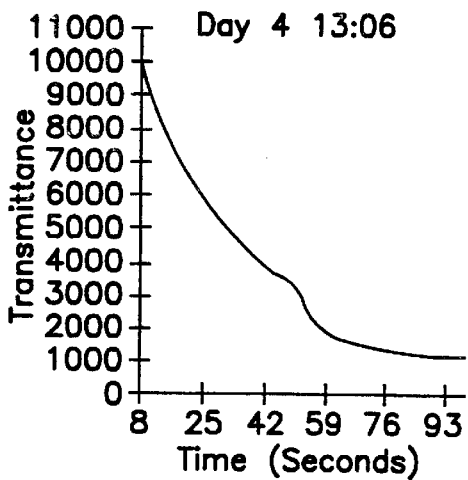
Figure 3D:
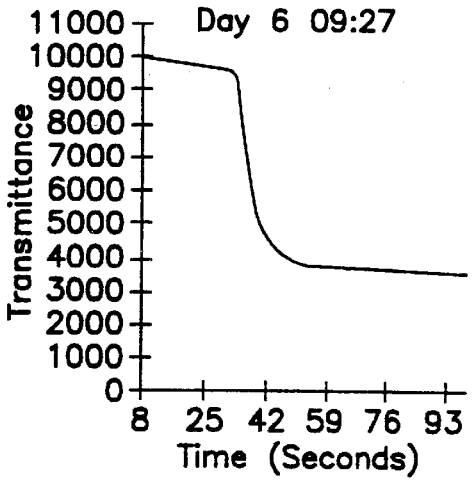
Figure 4A:
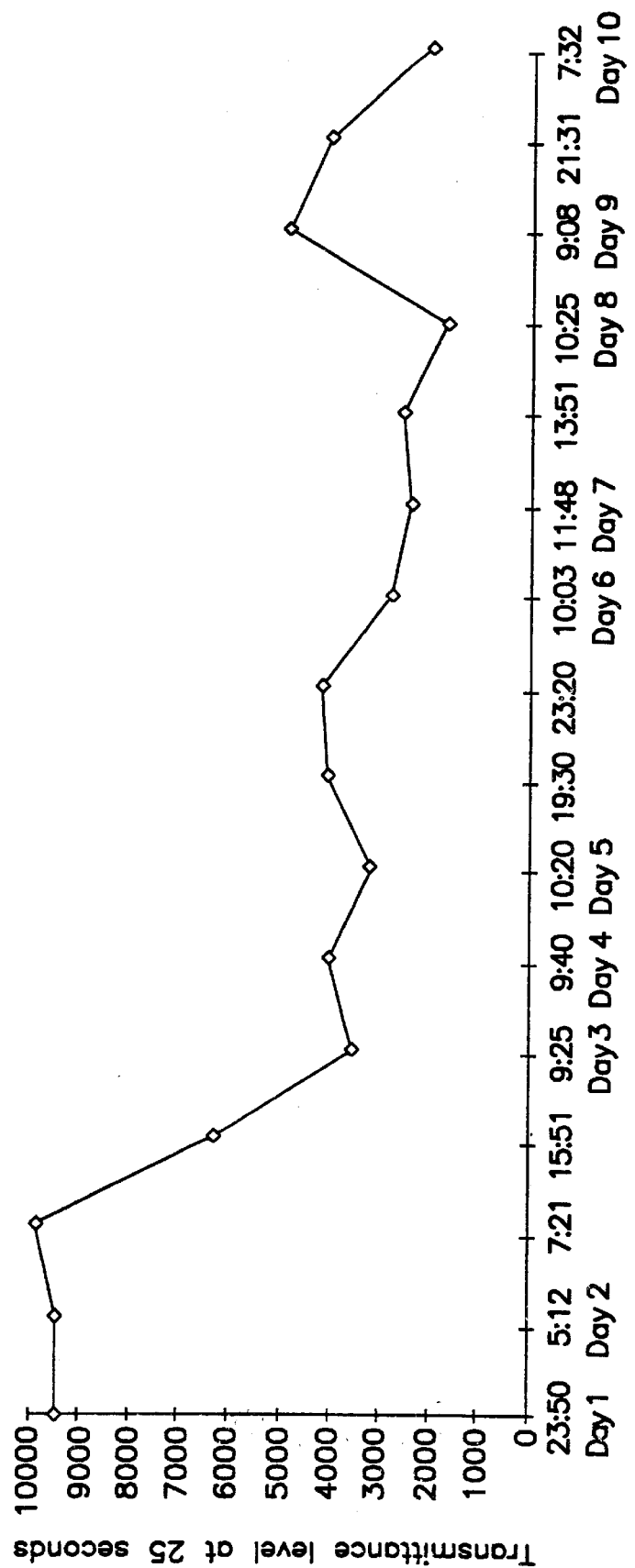
FIG. 4 illustrates serial transmittance levels (upper panel) and waveforms (lower panel) on a patient who developed DIC following trauma and died.
Figure 4B:
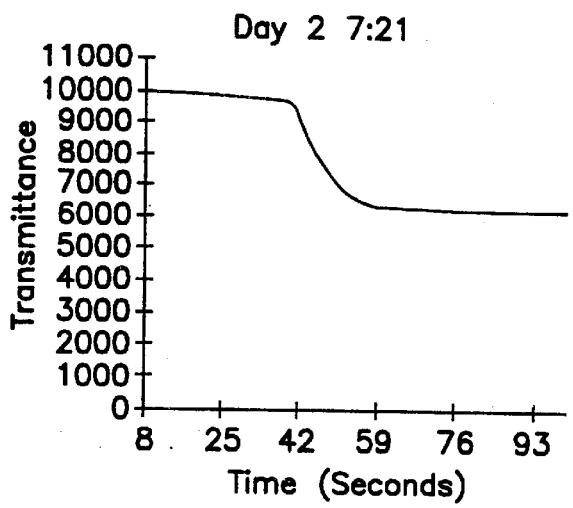
Figure 4C:
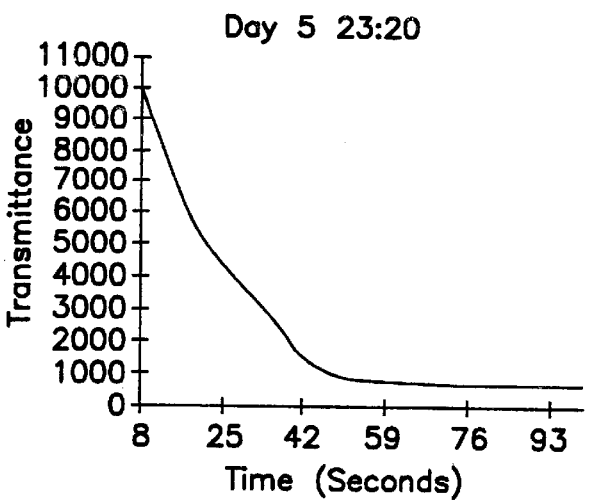
Figure 4D:
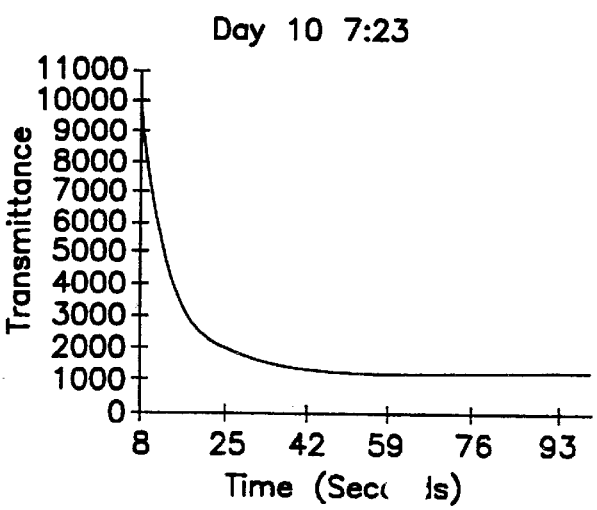

The positive predictive value of the test was 74%, which increased with increasing steepness of the bi-phasic slope and decreasing levels of light transmittance (Table 2 and FIG. 2). In the first two days of the study, there were 12 patients who had an abnormality in the clotting tests plus elevation of D-dimer levels. These were patients who were clinically recovering from DIC that occurred in the week preceding the study. This led to the impression that TW changes might correlate more closely with clinical events than the standard markers of DIC.

bility. FIG. 3 illustrates the results of a patient who initially presented with peritonitis following bowel perforation. This was further complicated by gram negative septicaemia postoperatively with initial worsening of DIC followed by a gradual recovery after appropriate therapy. As DIC progressed initially, there was increasing steepness in the bi-phasic slope of the TW and a fall in the light transmittance level. A reversal of this heralded clinical recovery. FIG. 4 illustrates the results of a patient who sustained severe internal and external injuries following a jet-ski accident. Although initially stabilized with blood product support, his condition deteriorated with continuing blood loss and development of fulminant DIC. The bi-phasic slope became increasingly steep with falls in transmittance level as the consequences of his injuries proved fatal. As DIC can arise from a variety of primary disorders, the clinical and laboratory manifestations can be extremely variable not only from patient to patient but also in the same patient with time. There is therefore, a need for systems that are not only robust in their diagnosis but simple and rapid to perform. Although it has been shown that the bi-phasic TW appeared to be sensitive for Haemostatic Dysfunction (e.g. DIC) and was not seen in other selected patient groups with coagulation aberrations or influenced by either (i) pre-analytical variables, (ii) different silica-based APTT reagents, (iii) the use of thrombin as the initiator of the coagulation reaction or (iv) treatment in the form of heparin or plasma expanders, the robustness of this assay for DIC could only be addressed through a prospective study. This study has shown that the bi-phasic TW provides diagnostic accuracy in DIC with an

TABLE 3

Serial results in a patient with sepsis

| Day | Time | PT (11.2–15s) | APTT (23–35s) | TT (10.5–15.5s) | Fgn (1.5–3.8 g/l) | D-Dimer (<0.5 mg/l) | Plt (150–400 × 10*/l) | TW |
|---|---|---|---|---|---|---|---|---|
| 1 | 0923 | 14.7 | 32.9 | 12.0 | 4.7 | 0.00 | 193 | B* |
| 1 | 2022 | 20.8* | 38.6* | 12.4 | 5.7 | 6.00* | 61* | B* |
| 2 | 0920 | 18.0* | 33.0 | 13.0 | 5.2 | 2.00* | 66* | N |
| 3 | 1011 | 16.3* | 24.8 | 13.2 | 4.7 | 0.00 | 64* | N |

PT = Prothrombin time,
APTT = Activated Partial thromoplastin Time,
TT = Thromoin Time,
Fgn = Fibrinogen,
Plt = Platelet count,
TW = Transmittance Waveform
*Indicates abnormal charges.
B = bi-phasic;
N = normal The availability of more than 3 sequential samples in 22 patients allowed for further assessment. Table 3 illustrates one such example with serial test results from a patient with *E. coli* septicaemia.

The appearance of a bi-phasic TW preceded changes in the standard tests for the diagnosis of DIC. It was only later in the day that the PT, APTT, Plt and D-dimer levels became abnormal and fulfilled the diagnostic criteria of DIC. Treatment with intravenous antibiotics led to clinical improvement by Day 2 with normalization of her TW in advance of the standard parameters of DIC. D-dimers and Plt were still respectively abnormal 24 and 48 hours later.

This correlation between clinical events and TW changes was seen in all the DIC patients where samples were available to chart the course of clinical events. As the TW changes were quantifiable and standardizable through recording of the transmittance level at 25 seconds, this analysis provided a handle in assessing prognostic applicaoverall sensitivity of 97.6% and specificity of 98%. In contrast, none of the standard parameters on an individual basis (i.e., PT, APTT, TT, Fgn, Plt, D-dimers) or even in combination, has ever reached the degree of sensitivity or specificity. The ready availability of TW data from the MDA-180 would also fulfil the criteria of simplicity and rapidity unlike the measurements of thrombin-antithrombin complexes or other markers that are dependent on ELISA technology. In addition, the advantages of TW analysis are that: (a) the bi-phasic TW chance appears to be the single most useful correlate within an isolated sample for DIC and as such, reliance need no longer be placed on serial estimations of a battery of tests, and (b) the appearance or resolution of the bi-phasic TW can precede changes in the standard, traditional parameters monitored in DIC with strong, clear correlation to clinical events and outcome.

Although the bi-phasic TW was also seen in patients who did not have DIC per se as defined by the above criteria, the clinical conditions were associated with Haemostatic Dysfunction—namely activated coagulation prior to initiation of clot formation resulting in a biphasic waveform (for example in chronic liver disease or in the very ill patients on the Intensive Care Unit who had multiple organ dysfunction). It appears that bi-phasic TW is sensitive to non-overt or compensated DIC and that a transmittance level of less than 90% (FIG. 2) or sequential falls in that level (FIG. 4), reflects decompensation towards a more overt manifestation and potentially fulminant form of DIC. This line of explanation is supported by the observation of only a mild bi-phasic TW (transmittance level of about 95%) in 2 patients with atrial fibrillation; a condition that is associated with mild coagulation activation and elevated D-dimer levels. As no follow-up samples were available on these 2 patients whose clinical details were otherwise unremarkable, their bi-phasic TW could well have been transient. Nonetheless, these cases illustrate that the lower the level of light transmittance, the more likely the bi-phasic TW becomes predictive of Haemostatic Dysfunction, particularly DIC.

The observation of a normal TW in a patient with PET and DIC needs further exploration as the study did not selectively aim to examine any particular patient groups and only had a total of 6 patients with PET; the remaining 5 of which did not have DIC. One explanation which would be supported by other findings in this study is that the patient could have been recovering from PET and DIC at the time of the sample. There may already have been normalization in the bi-phasic TW in advance of the other parameters which were still abnormal and indicative of DIC. Another explanation is that the disturbed haemostatic process in PET is more localized and different from the DIC that arises from other conditions. Such patients respond dramatically to delivery of the fetus which suggests anatomical localization of the pathological process to the placenta despite standard laboratory clotting tests implying systemic evidence of the condition.

EXAMPLE

Though analysis of the transmittance at a time of 25 seconds is helpful in predicting DIC, a second embodiment of the invention has been found that greatly improves sensitivity and specificity. It has been found that looking at transmittance at a particular time can result in detecting an artifact or other decrease in transmittance at that point, even though the waveform is not a bi-phasic waveform. For example, a temporary dip in transmittance at 25 seconds would cause such a patient sample to be flagged as bi-phasic, even if the waveform was normal or at least not bi-phasic. Also, if a patient sample had a particularly short clotting time, then if clot formation begins e.g. prior to 25 seconds (or whatever time is preselected), then the waveform could be flagged as biphasic, even though the real reason for decreased transmittance at 25 seconds is because clot formation has already begun/occurred.

Figure 9:
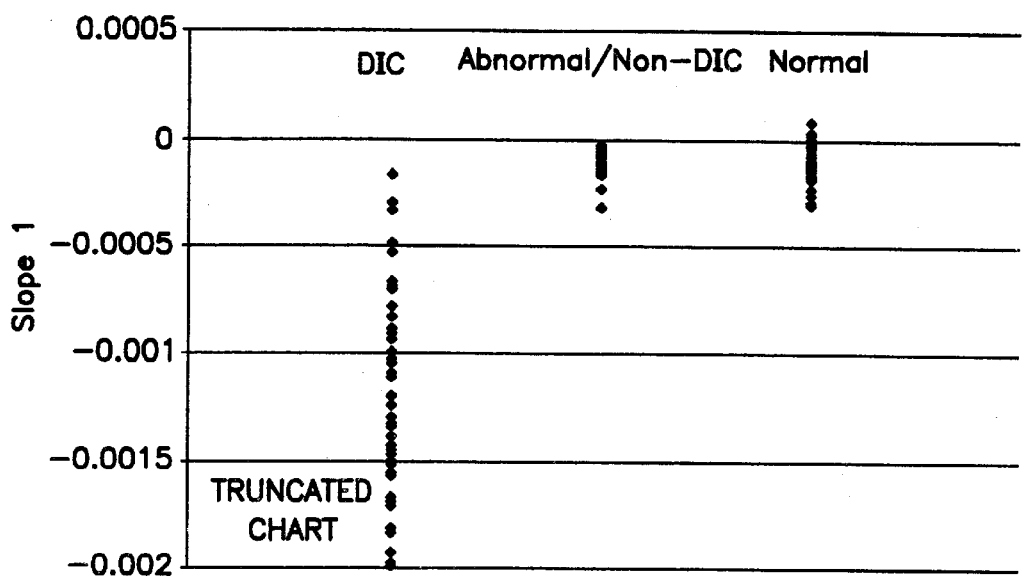
FIGS. 9 and 11 show partial subpopulations of the data shown in FIGS. 8 and 10.
Figure 11:
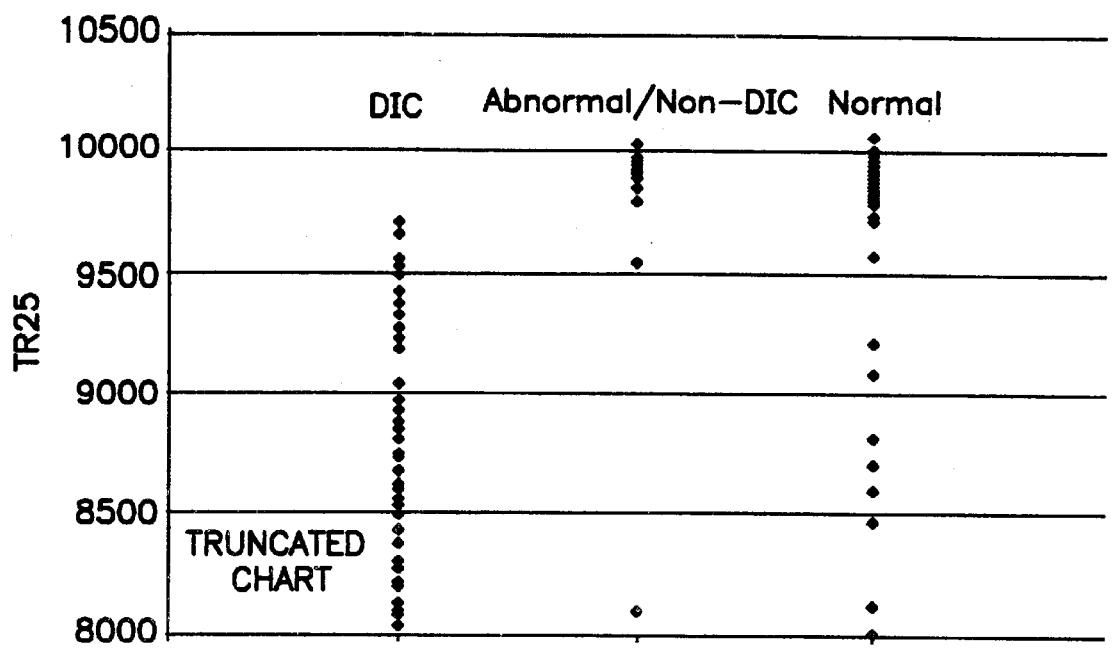

For this reason, it has been found that rather than analysis of transmittance at a particular time, it is desirable to calculate the slope of the waveform prior to initiation of clot formation. This calculation can involve determination of clot time followed by determination of waveform slope prior to clot time. In an additional embodiment, the slope (not transmittance) is determined prior to clot time or prior to a preselected time period, whichever is less. As can be seen in FIG. 11, when transmittance is used for determining e.g. DIC, there is poor specificity and sensitivity. However, as can be seen in FIG. 9, when slope prior to initiation of clot formation is used, specificity and sensitivity are greatly improved, and are better than standard tests used in the diagnosis of Haemostatic Dysfunction, such as DIC.

Figure 5:
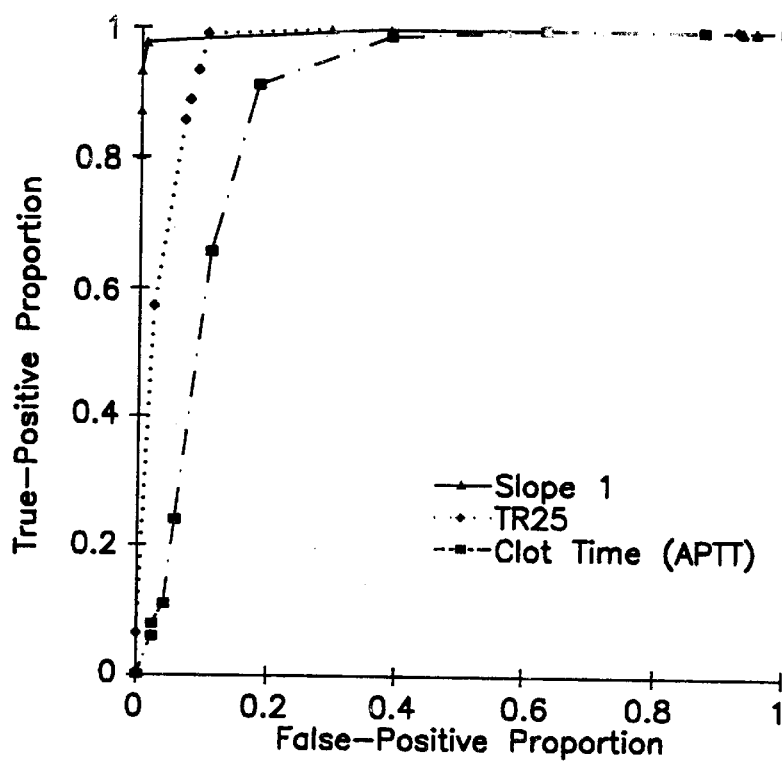
FIG. 5 illustrates ROC plots for the prediction of DIC transmittance at 25 seconds (TR25), APTT clot time, and slope__1 (the slope up to the initiation of clot formation)

Additional testing was performed on three sets of patients. The first set consisted of 91 APTT assays run on samples from 51 different confirmed DIC patients. The second set of data consisted of 110 APTT assays run on samples from 81 different confirmed normal patients. The third set of data included 37 APTT assays run on 22 abnormal, non-DIC samples. FIG. 5 illustrates ROC plots for the prediction of DIC for three different parameters derived from the APTT assay using the combined data sets described: (1) transmittance at 25 seconds (TR25), (2) APTT clot time, and (3) slope 1 (the slope up to initiation of clot formation). Slope 1 exhibited the best predictive power, followed by TR25. It has also been shown that transmittance at 18 seconds has predictive value, particularly when the APTT clot time is less than 25 seconds. The "cutoffs" associated with the highest efficiency for the three parameters are listed in Table 4:

TABLE 4

| Parameter | Cutoff |
| --- | --- |
| TR25 | <9700 |
| Clot Time | >35 |
| Slope 1 | <−0.0003 |

Figure 6:
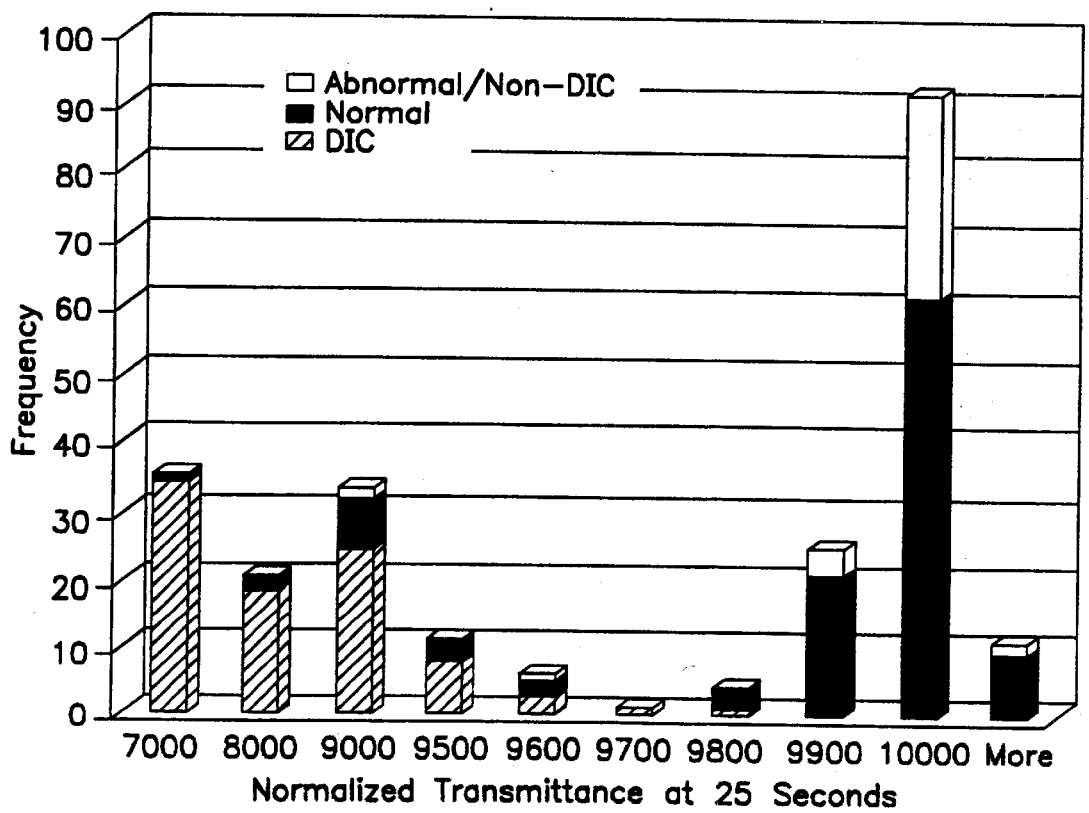
FIGS. 6 and 7 show histograms for DIC, normal and abnormal/non-DIC populations for TR25 and slope__1.
Figure 7:
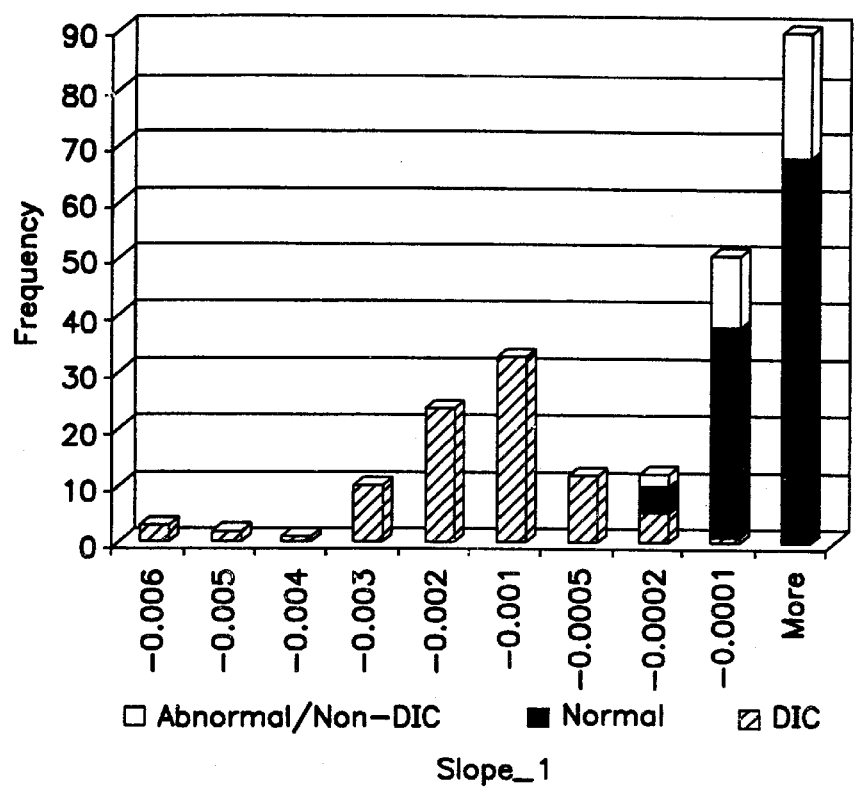

It should be noted that these cutoffs have shifted with the addition of the third set, and would likely shift again, depending on the sample populations. FIGS. 6 and 7 show the histograms for the DIC, normal and abnormal/non-DIC populations for TR25 and slope 1 respectively. Tables 5 and 6 show the data for the histograms in FIGS. 6 and 7 respectively:

TABLE 5

| Bins | DIC | Normal | Abnormal/Non-DIC |
| --- | --- | --- | --- |
| −0.006 | 3 | 0 | 0 |
| −0.005 | 2 | 0 | 0 |
| −0.004 | 1 | 0 | 0 |
| −0.003 | 10 | 0 | 0 |
| −0.002 | 24 | 0 | 0 |
| −0.001 | 33 | 0 | 0 |
| −0.0005 | 12 | 0 | 0 |
| −0.0002 | 5 | 5 | 2 |
| −0.0001 | 1 | 37 | 13 |
| More | 0 | 68 | 22 |

TABLE 6

| Bin | DIC | Normal | Abnormal/Non-DIC |
| --- | --- | --- | --- |
| 7000 | 34 | 1 | 0 |
| 8000 | 18 | 2 | 0 |
| 9000 | 26 | 6 | 1 |
| 9500 | 8 | 3 | 0 |
| 9600 | 3 | 2 | 1 |
| 9700 | 1 | 0 | 0 |
| 9800 | 1 | 3 | 0 |
| 9900 | 0 | 21 | 4 |
| 10000 | 0 | 62 | 30 |
| More | 0 | 10 | 1 |

Figure 8:
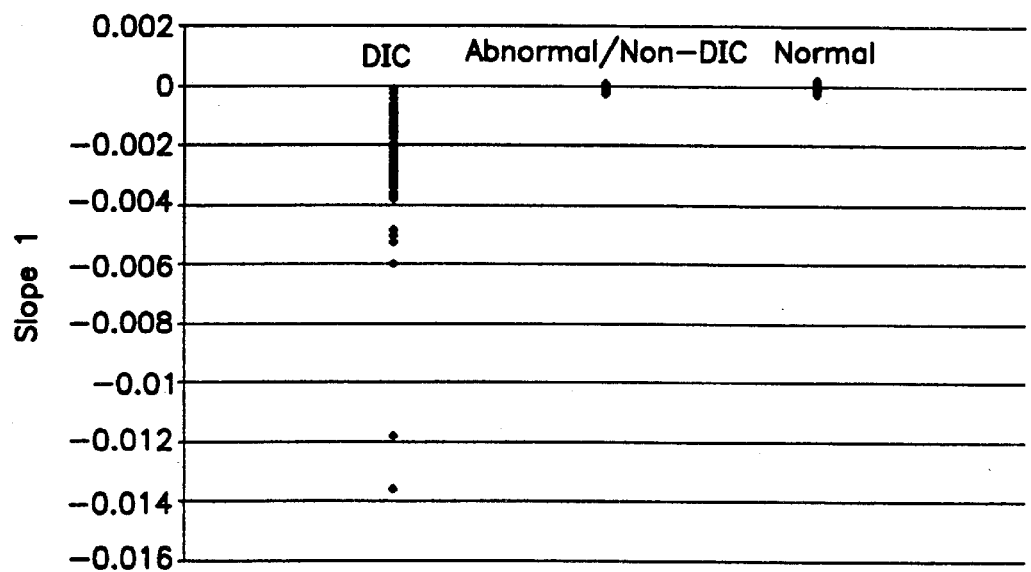
FIGS. 8 and 10 show group distributions for slope__1 and TR25 respectively.
Figure 10:
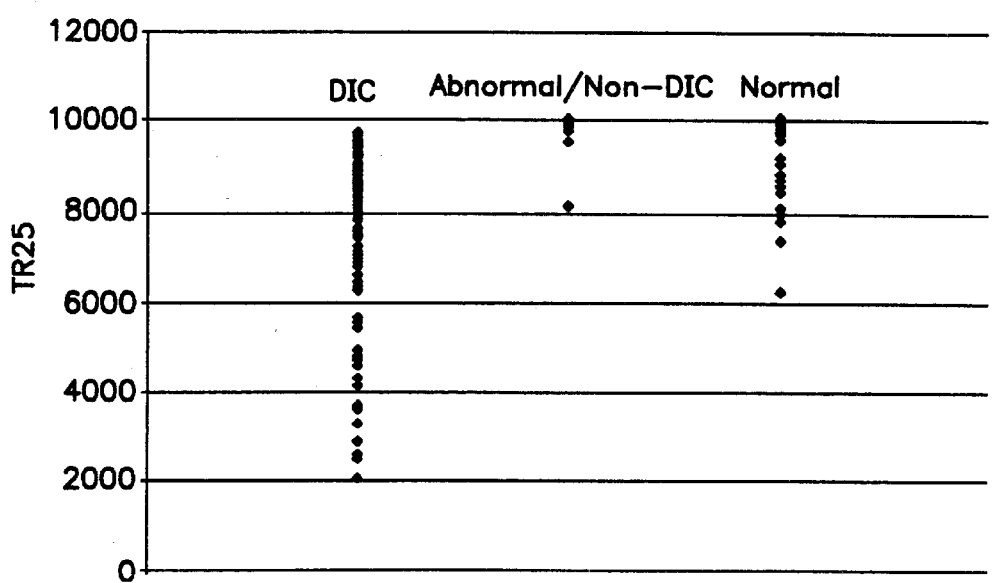

FIGS. 8 and 10 show the group distributions for Slope 1 and TR25 respectively; and FIGS. 9 and 11 show the group distributions for Slope 1 and TR25 respectively. FIGS. 9 and 11 show partial subpopulations of the data shown in FIGS. 8 and 10.

When the prediction of Haemostatic Dysfunction is performed on an automated or semi-automated analyzer, the detected bi-phasic waveform can be flagged. In this way, the operator of the machine, or an individual interpreting the test results (e.g. a doctor or other medical practitioner) can be alerted to the existence of the biphasic waveform and the possibility/probability of Haemostatic Dysfunction such as DIC. The flag can be displayed on a monitor or printed out. A slope of less than about −0.0003 or less than about −0.0005 is the preferred cutoff for indicating a bi-phasic waveform. An increasing steepness in slope prior to clot formation correlates to disease progression.

The above examples show that waveform analysis on the APTT assay can identify characteristic bi-phasic patterns in patients with haemostatic dysfunction. In the majority of cases, this dysfunction could be labelled as DIC. This diagnostic waveform profile was seen in all APTT reagents tested, which were either silica or ellagaic acid-based. It has also been surprisingly found that a bi-phasic waveform can also be seen on PT assays with particular reagents, and that the bi-phasic waveform is likewise indicative of haemostatic dysfunction, primarily DIC.

Using samples that give bi-phasic APTT waveforms, the PT waveform profile was derived using PT reagents (thromboplastin), namely Recombiplast™ (Ortho), Thrombrel™ (Dade-Behring) and Innovin™ (Dade-Behring). Both Recombiplast and Thrombrel were particularly good at showing bi-phasic responses. Innovin was intermediate in its sensitivity. Using the transmittance level at 10 seconds into the PT reaction as the quantitative index, Recombiplast and Thrombrel objectively showed lower levels of light transmittance than Innovin. Thrombrel can show a slight increase in initial light transmittance before the subsequent fall. This may be, in part, related to the relative opaqueness of Thrombrel.

Figure 12:
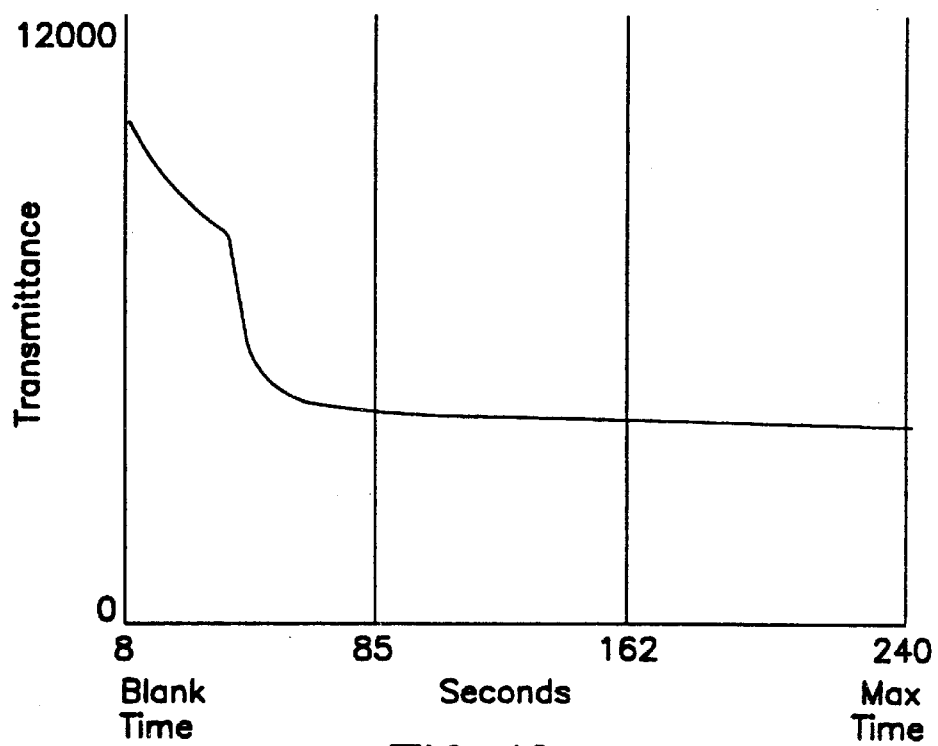
FIG. 12 is an optical transmission profile for an APTT assay.
Figure 13:
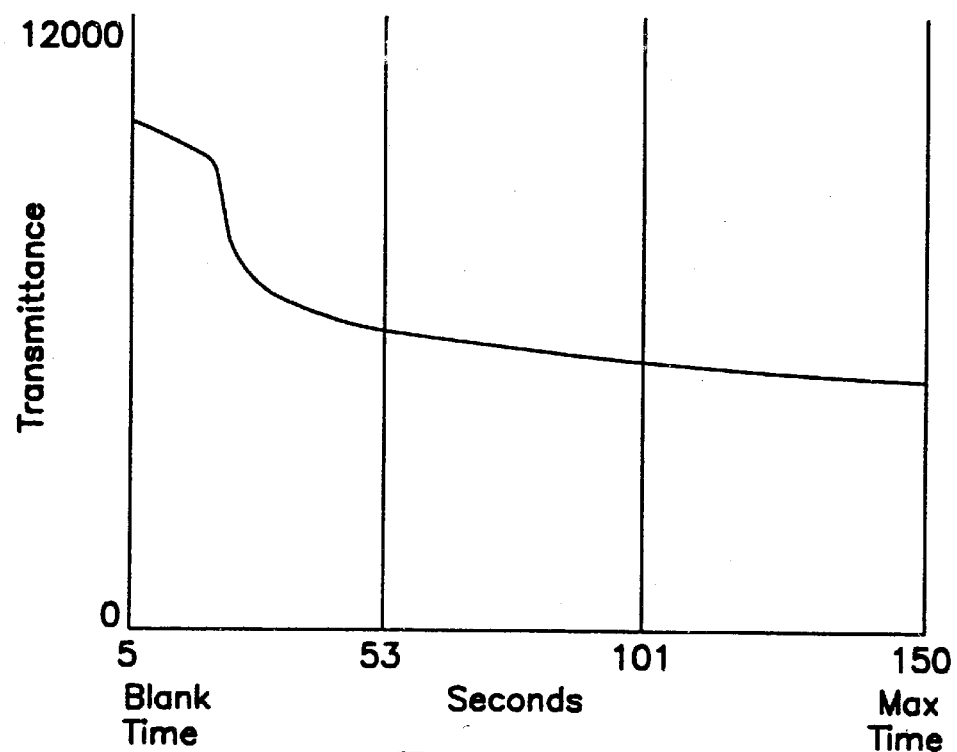
FIGS. 13 and 14 are optical transmission profiles for PT assays.
Figure 14:
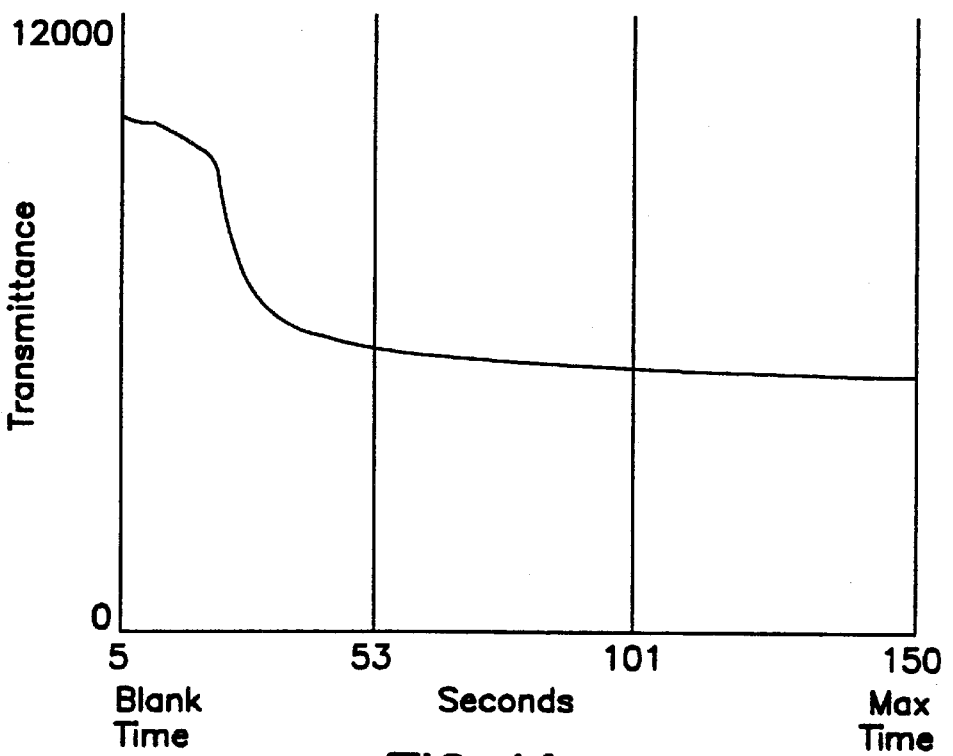

Further studies were performed comparing APTT profiles using Platelin™ and PT waveform profiles using Recombiplast™. Consecutive samples over a four week period from the intensive care unit were assessed. Visually, and on objective scores (comparing TL18 for APTT and TL10 for PT), the APTT profile was more sensitive to changes of haemostatic dysfunction and clinical progression than the PT profile. This relative sensitivity can be seen in the APTT profile of FIG. 12 (Platelin) compared to the PT profiles of FIG. 13 (Recombiplast) and FIG. 14 (Thromborel S). Invariably, at smaller changes in light transmittance, the APTT waveform detected abnormalites more easily than the PT waveform. Nonetheless, in severe degrees of haemostatic dysfunction, both bi-phasic profiles were concordant.

In a further embodiment of the invention, the time dependent measurement, such as an optical transmittance profile, can be performed substantially or entirely in the absence of clot formation. In this embodiment, a reagent is added which causes the formation of a precipitate, but in an environment where no fibrin is polymerized. The reagent can be any suitable reagent that will cause the formation of a precipitate in a sample from a patient with haemostatic dysfunction, such as DIC. As an example, divalent cations, preferably of the transition elements, and more preferably calcium, magnesium, manganese, iron or barium ions, can be added to a test sample. These ions cause activation of an atypical waveform that can serve as an indicator of haemostatic dysfunction. It is also possible to run this assay in the absence of a clotting reagent (APTT, PT, or otherwise). As part of the reagent that comprises the activator of the atypical waveform, or separately in another reagent, can also be provided a clot inhibitor. The clot inhibitor can be any suitable clot inhibitor such as hirudin, PPACK, heparin, antithrombin, I2581, etc. The formation of the atypical waveform can be monitored and/or recorded on an automated analyzer capable of detecting such a waveform, such as one that monitors changes in turbidity (e.g. by monitoring changes in optical transmittance).

Figure 15:
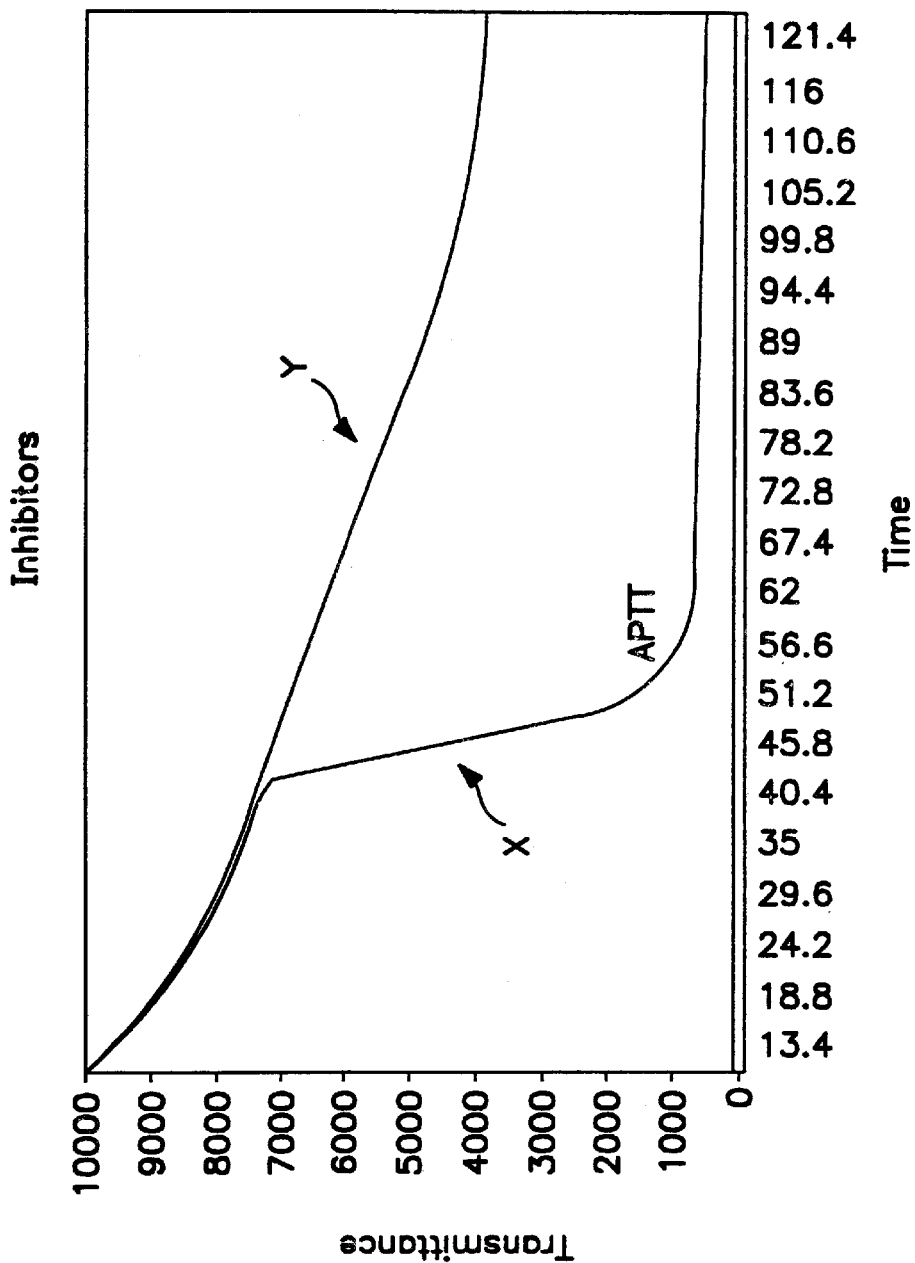
FIG. 15 is an illustration of two waveforms where (x) is a test run on a sample using an APTT clotting reagent and resulting in a biphasic waveform, and (y) is a test run where a clot inhibitor is used.
Figure 16:
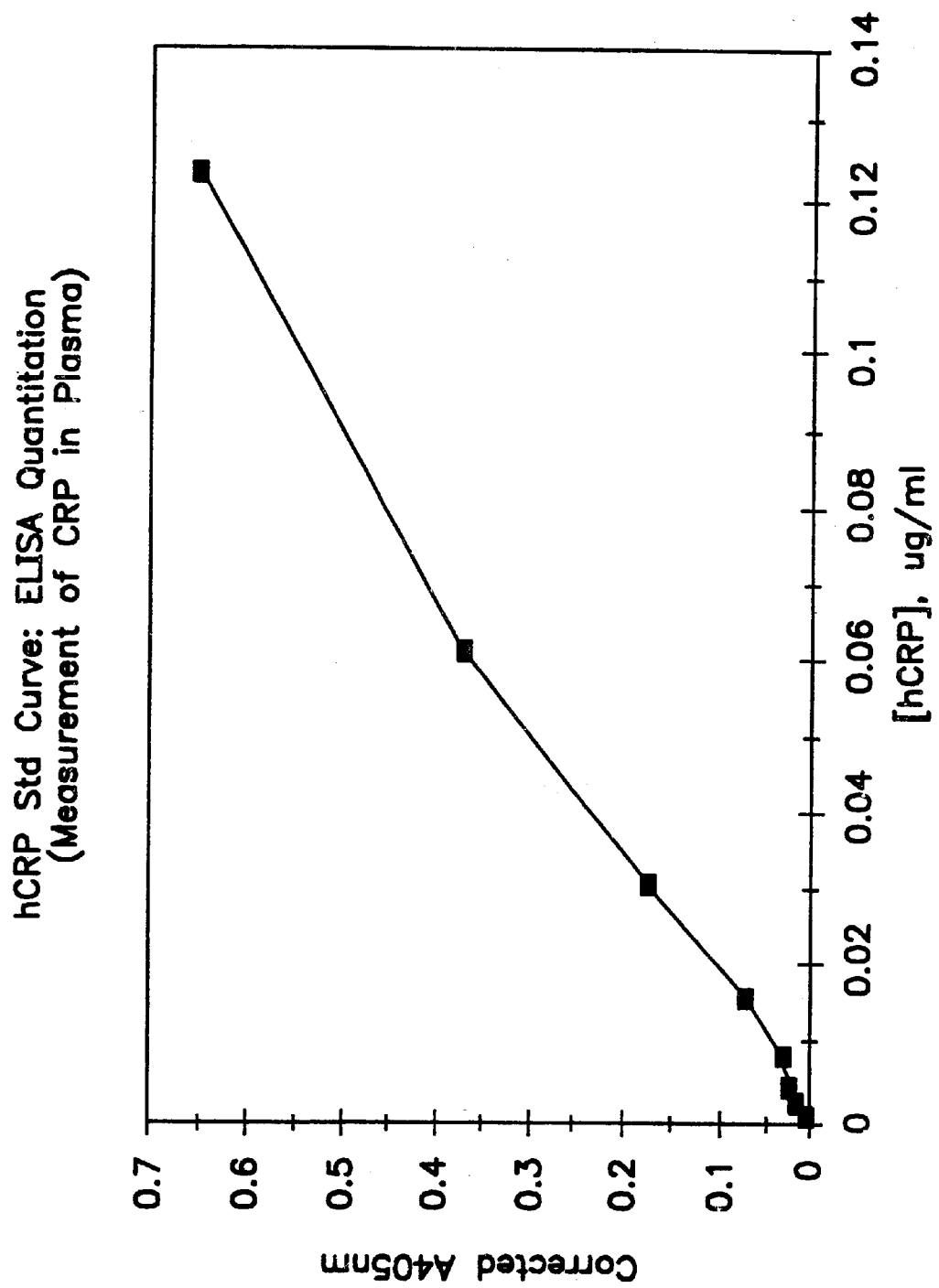
FIG. 16 is a standard curve for ELISA of CRP.

FIG. 15 is an illustration of two waveforms: waveform (x) is a test run on a sample using an APTT clotting reagent and resulting in an atypical (biphasic) waveform, whereas waveform (y) is a test run on a sample where a clot inhibitor is used (along with a reagent, such as a metal divalent cation, which causes the formation of a precipitate in the sample). Waveform (y) is exemplary of a waveform that can result in patients with haemostatic dysfunction where no clotting reagent is used and/or a clot inhibitor is added prior to deriving the time-dependent measurement profile. Generally speaking, the greater the slope of the waveform (the larger the drop in transmittance in the same period of time) due to the precipitate formation, the greater severity of the patient's haemostatic dysfunction. FIG. 16 is a standard curve for ELISA of CRP (CRP isolated from a patient used as the standard).

The precipitate formed in the present invention was isolated and characterized by means of chromatography and purification. Gel Filtration was performed as follows: A column (Hiprep Sephacryl S-300 High resolution—e.g. resolution of 10 to 1500 kDa) was used.

Figure 17:
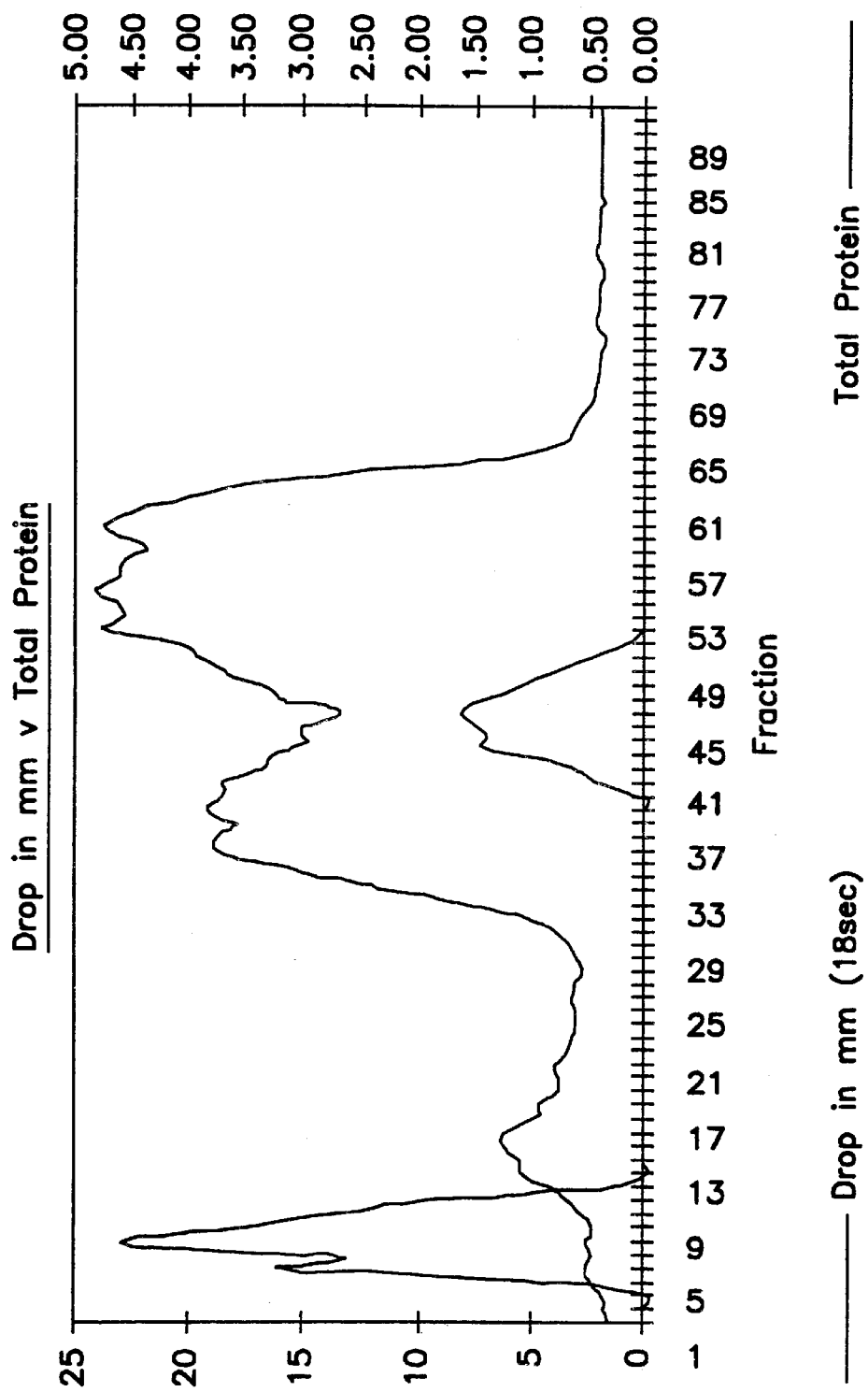
FIG. 17 shows an isolated precipitate after gel filtration.

The volume was 320 ml (d=26 mm, l=600 mm), and the flow rate was 1.35 ml/min. FIG. 17 shows the isolated precipitate.

Figure 18:
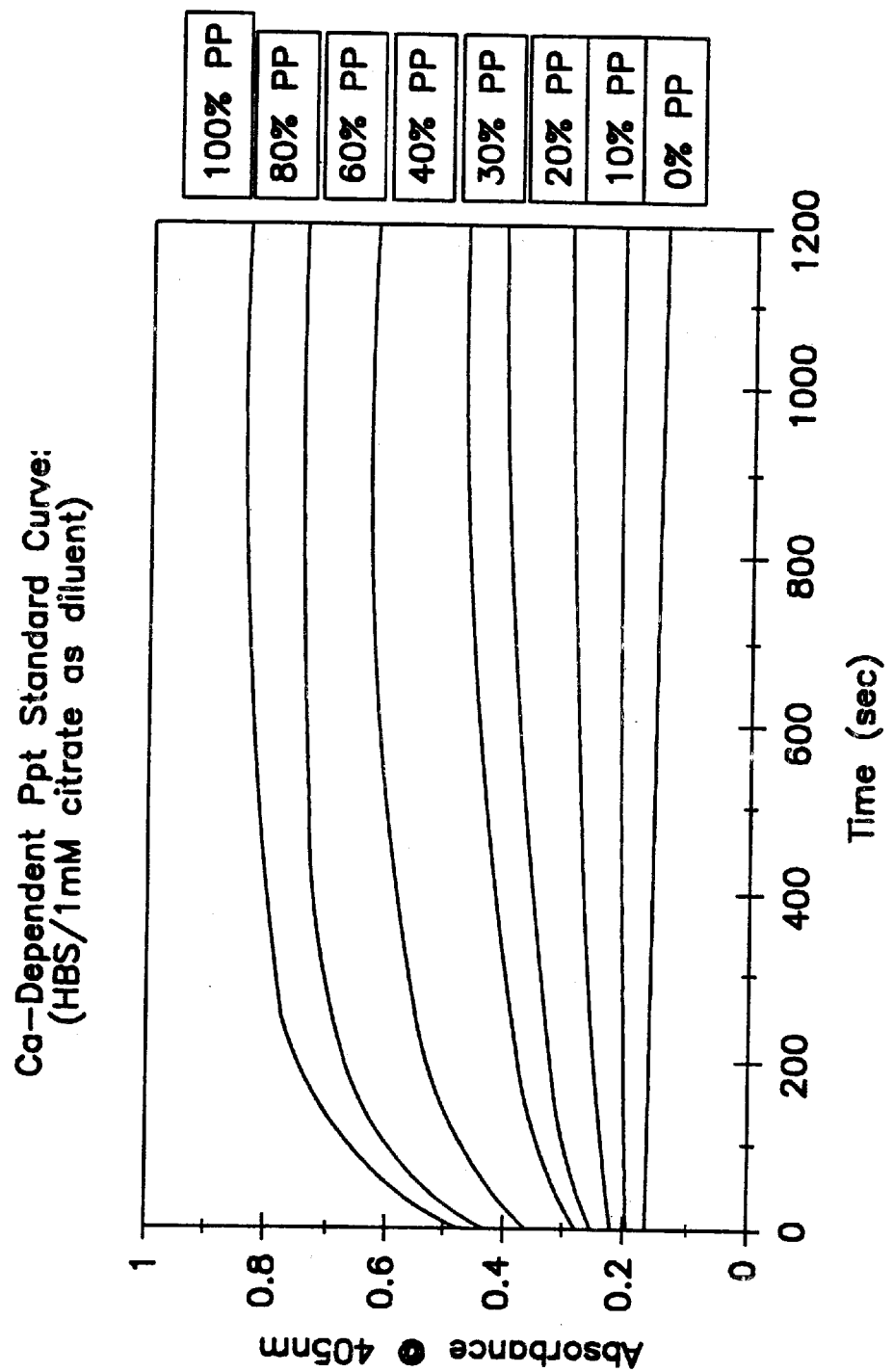
FIG. 18 is a graph showing the time course of turbidity in a sample upon adding a precipitate inducing reagent.
Figure 19:
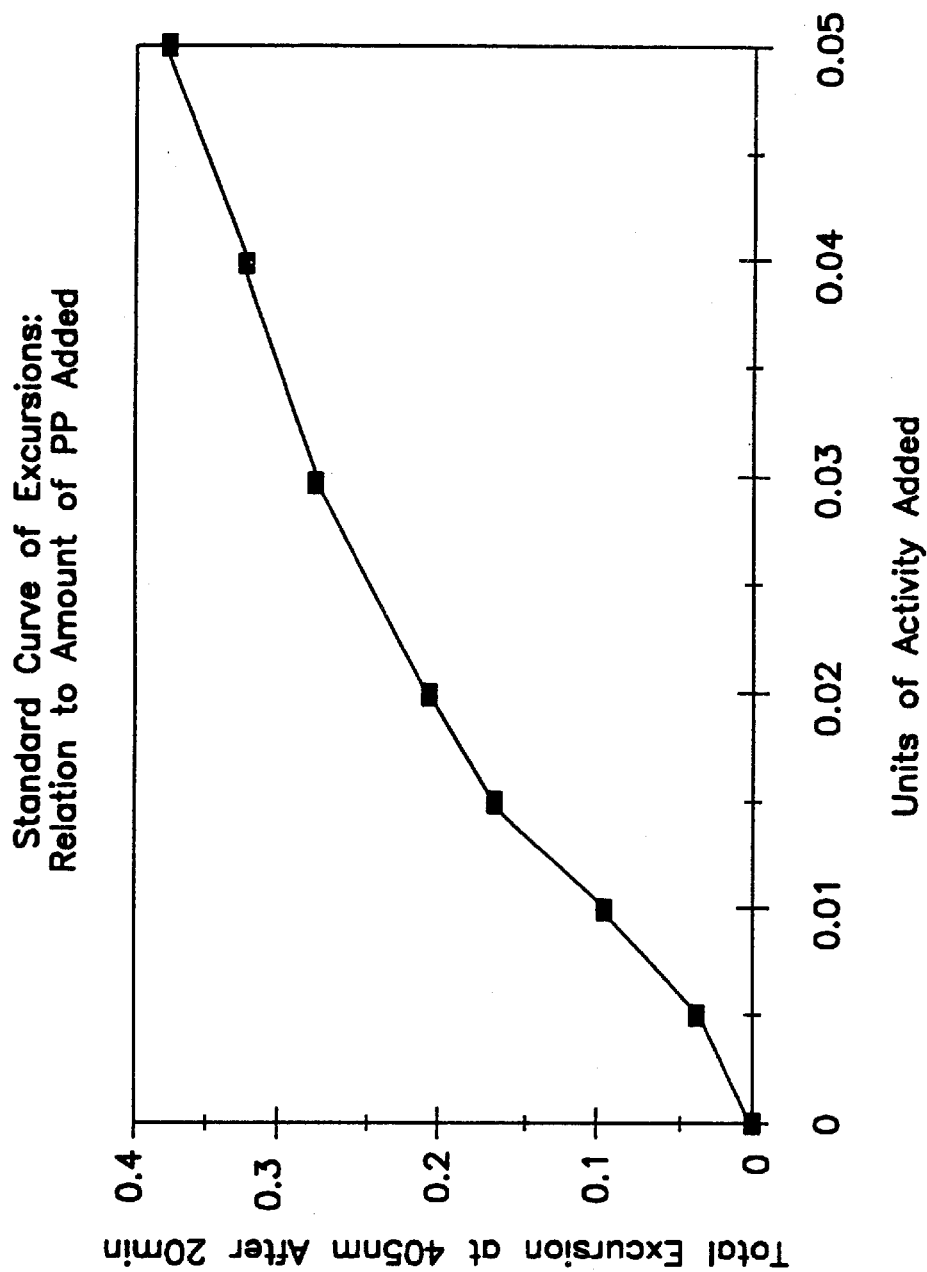
FIG. 19 is a graph showing the relationship between maximum turbidity change and amount of patient plasma in a sample.

FIG. 18 is a graph showing the time course of turbidity in a sample upon adding a precipitate inducing agent (in this case divalent calcium) and a thrombin inhibitor (in this case PPACK) to mixtures of patient and normal plasmas. FIG. 19 is a graph showing the relationship between maximum turbidity change and amount of patient plasma in one sample. 0.05 units implies 100% patient plasma. (Data from FIG. 18).

Figure 20:
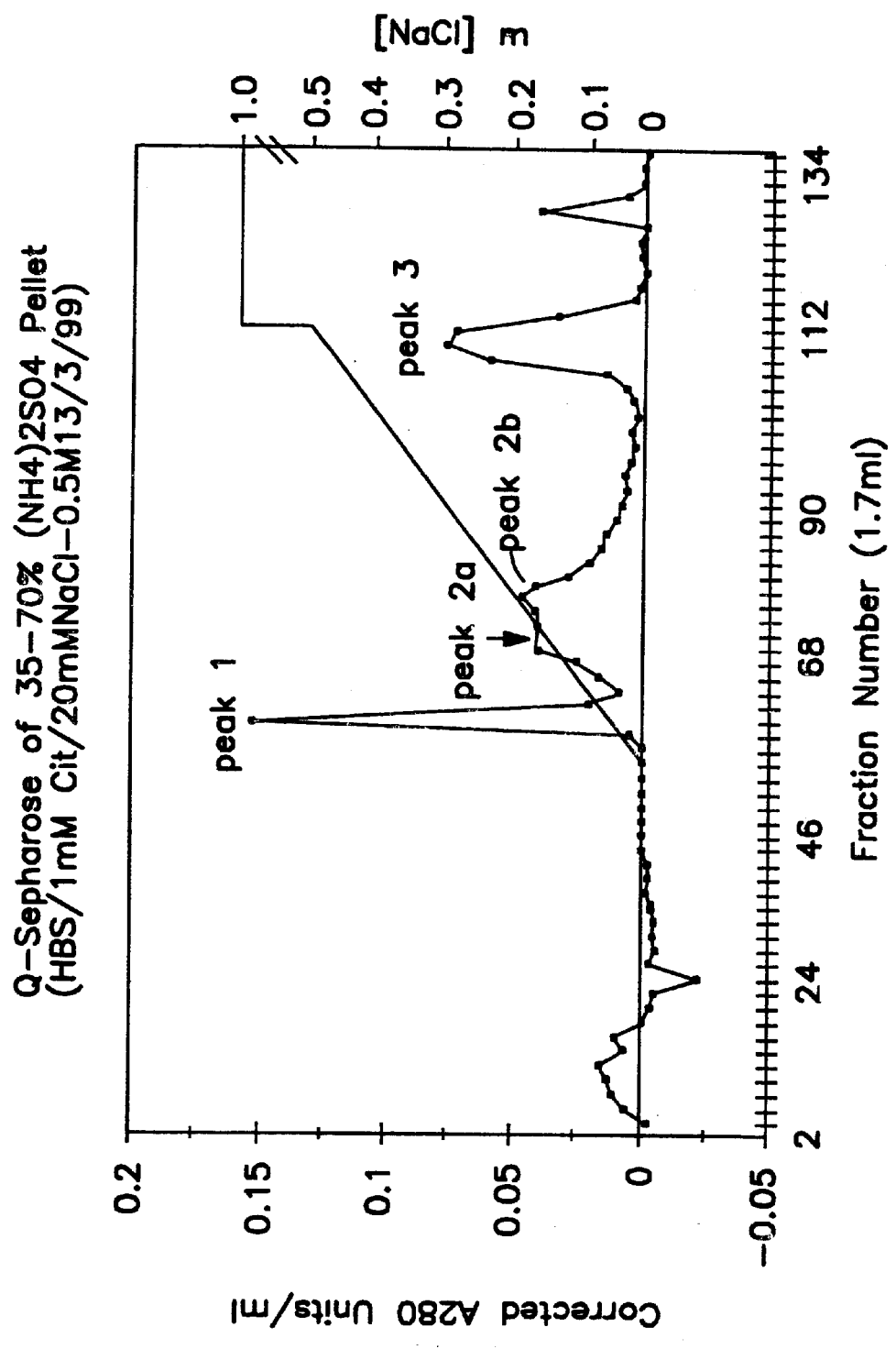
FIG. 20 shows the results of anion exchange chromatography of material recovery after fractionation of patient plasma.
Figure 2I:
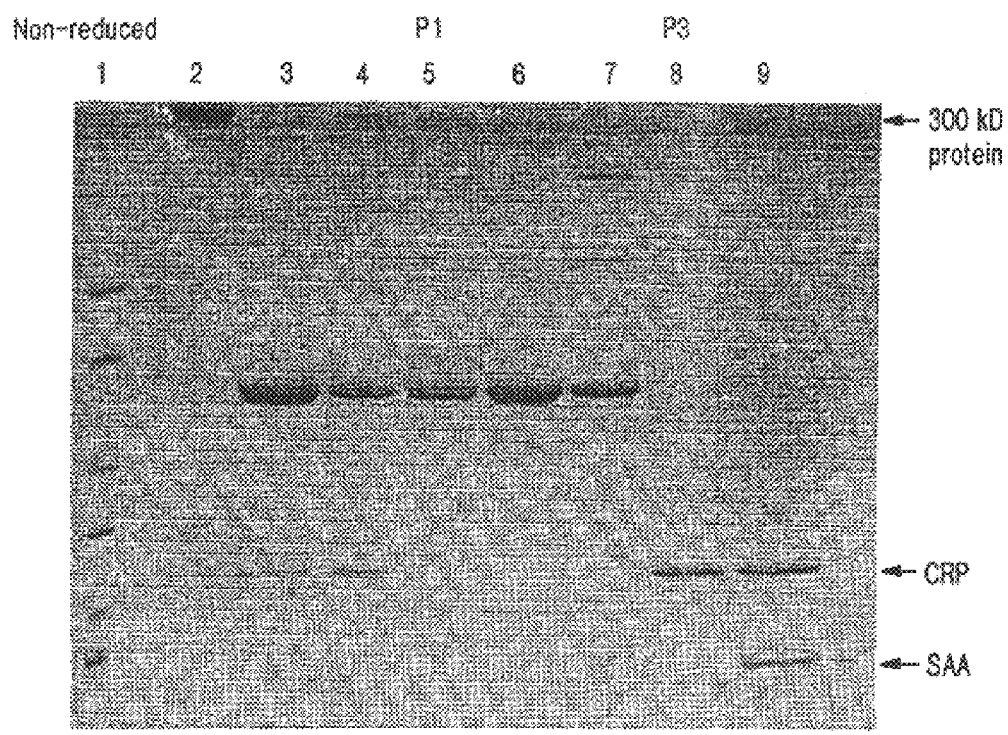
Figure 2I:
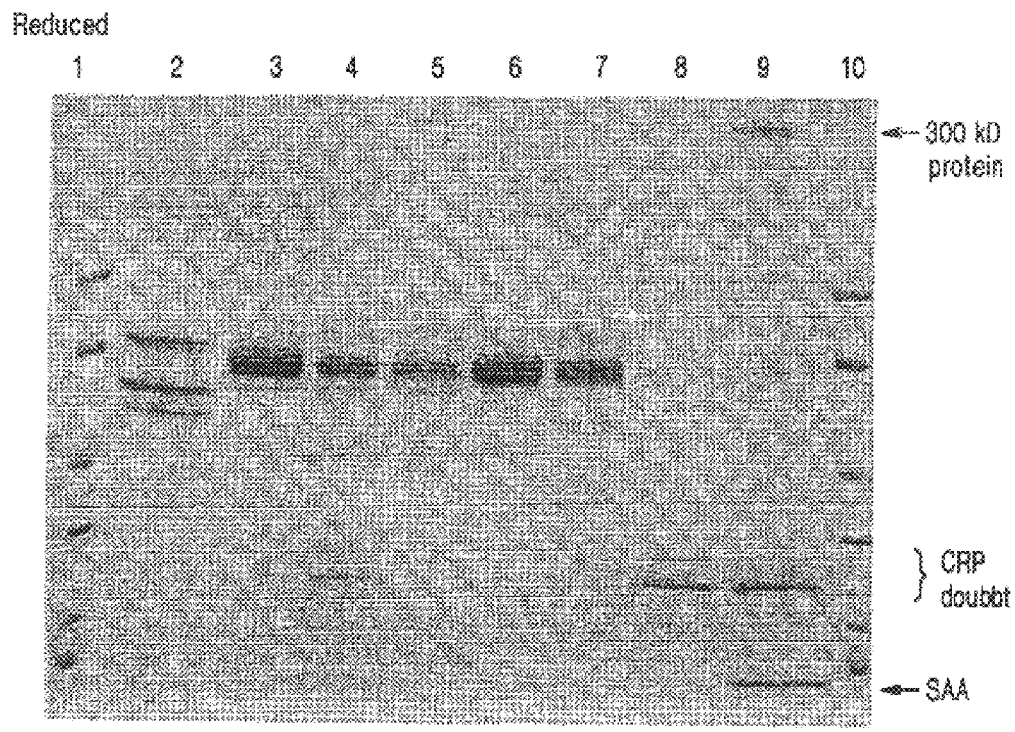

The steps used in the purification of components involved in the turbidity change in a patient's plasma were as follows: PPACK (10 $\mu$M) was added to patient plasma. Calcium chloride was added to 50 mM, followed by 8 minutes of incubation, followed b the addition of EtOH to 5%. The sample was then centrifuged 10,500×g for 15 minutes at 4 degrees Celsius. The pellet was then dissolved in HBS/1 mM citrate/10 $\mu$M PPACK, followed by 35–70% (NH$_4$)$_2$SO$_4$ fractionation. Finally, sepharose chromatography was performed using a 5 ml bed, 0.02–0.5M NaCl gradient and 50 ml/side, to collect 2 ml fractions. FIG. 20 shows the results of anion exchange chromatography (Q-sepharose) of material recovery after the 35–70% ammonium sulfate fractionation of patient plasma.

FIGS. 21a and 21b show the non-reduced and reduced, respectively, SDS PAGE of various fractions obtained upon fractionation of patient plasma. The loading orientation (left to right): 5–15% gradient/Neville Gel. (approximately 10 $\mu$g protein loaded per well). In lane 1 are molecular weight standard (94, 67, 45, 30, 20 and 14 kDa from top to bottom. In lane 2 is 35% (NH$_4$)$_2$SO$_4$ pellet, whereas in lane 3 is 70% (NH$_4$)$_2$SO$_4$ supernate. Lane 4 is Q-sepharose starting material. Also shown in FIGS. 21a and b are (from FIG. 20) peaks 1, 2a, 2b and 3 in, respectively, lanes 5, 6, 7 and 8. Lane 9 is pellet 1, whereas in lane 10 are again, molecular weight standards. Results of NH$_2$-terminal sequencing showed peak 3, the 22 kD protein in lanes 8 and 9 to be C-reactive protein (CRP), and the 10 kD protein in lane 9 to be human serum amyloid A (SAA). Peak 1 in lane 5 is a 300 kD protein which, as can be seen in FIG. 23, is part of the complex of proteins (along with CRP) in the precipitate formed due to the addition of a metal divalent cation to a plasma sample.

Figure 22:
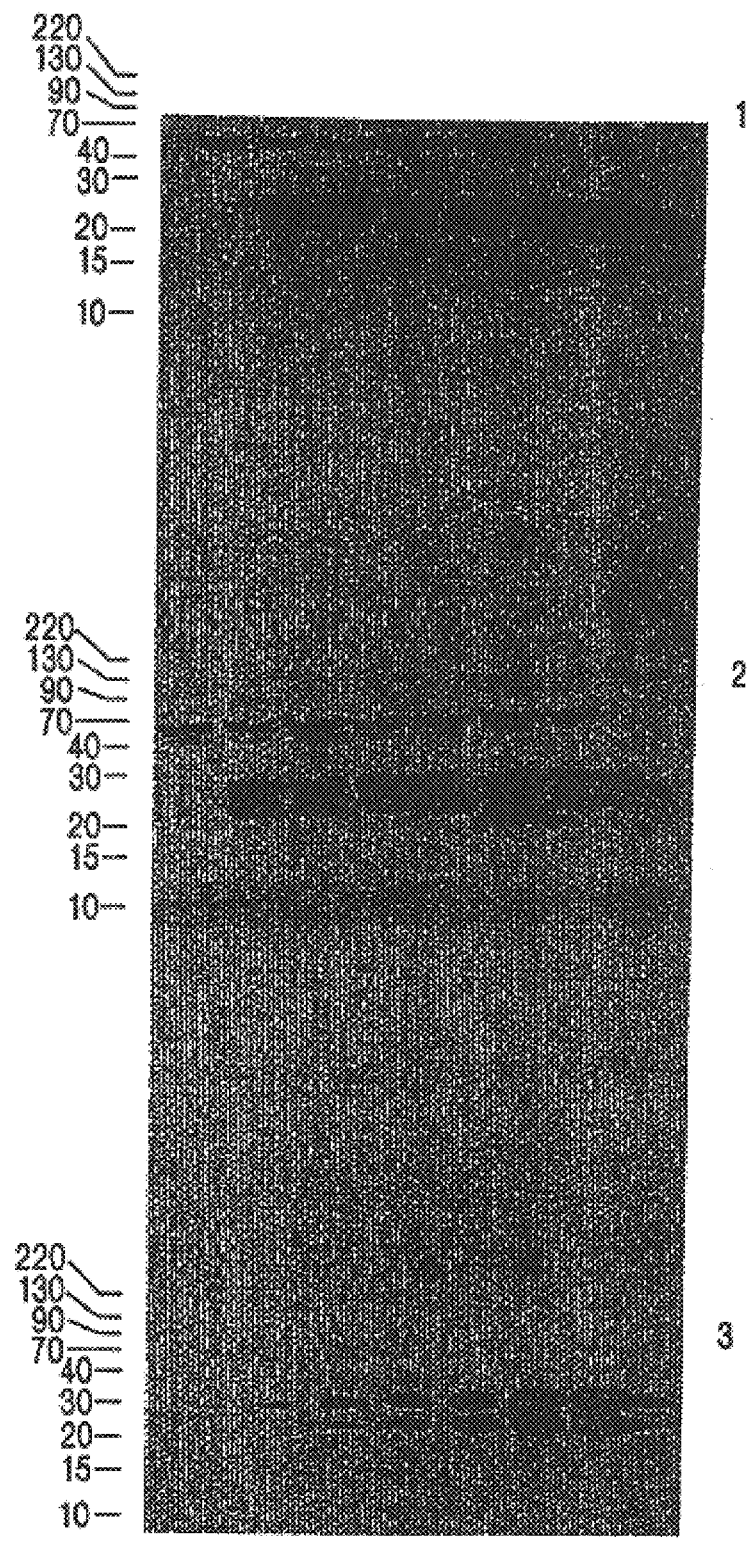
FIG. 22 shows immunoblots of CRP in normal and DIC plasma.

Immunoblots of CRP were performed in normal and DIC plasma. Blot 1 (see FIG. 22): (used 0.2 µl plasmas for reducing SDS-PAGE/CRP Immunoblotting). Loading orientation (left to right) NHP; Pt 5; 3; 1; 2; 4; and 8. For Blot 2: Loading orientation (left to right): NHP; Pt 9; 10; 11; 7; 6; 12. For Blot 3: (CRP purified from DIC patient plasma)— Loading orientation (left to right; ng CRP loaded): 3.91; 7.81; 15.625; 31.25; 62.5; 125; 250. The Blots were blocked with 2% (w/v) BSA in PBS, pH 7.4 and then sequentially probed with rabbit anti-human CRP-IgG (Sigma, Cat# C3527, dil 1:5000 in PBS/0.01% Tween 20) and then treated with the same antibody conjugated to HRP (dil 1:25000 in PBS/0.01% Tween 20).

Figure 23:
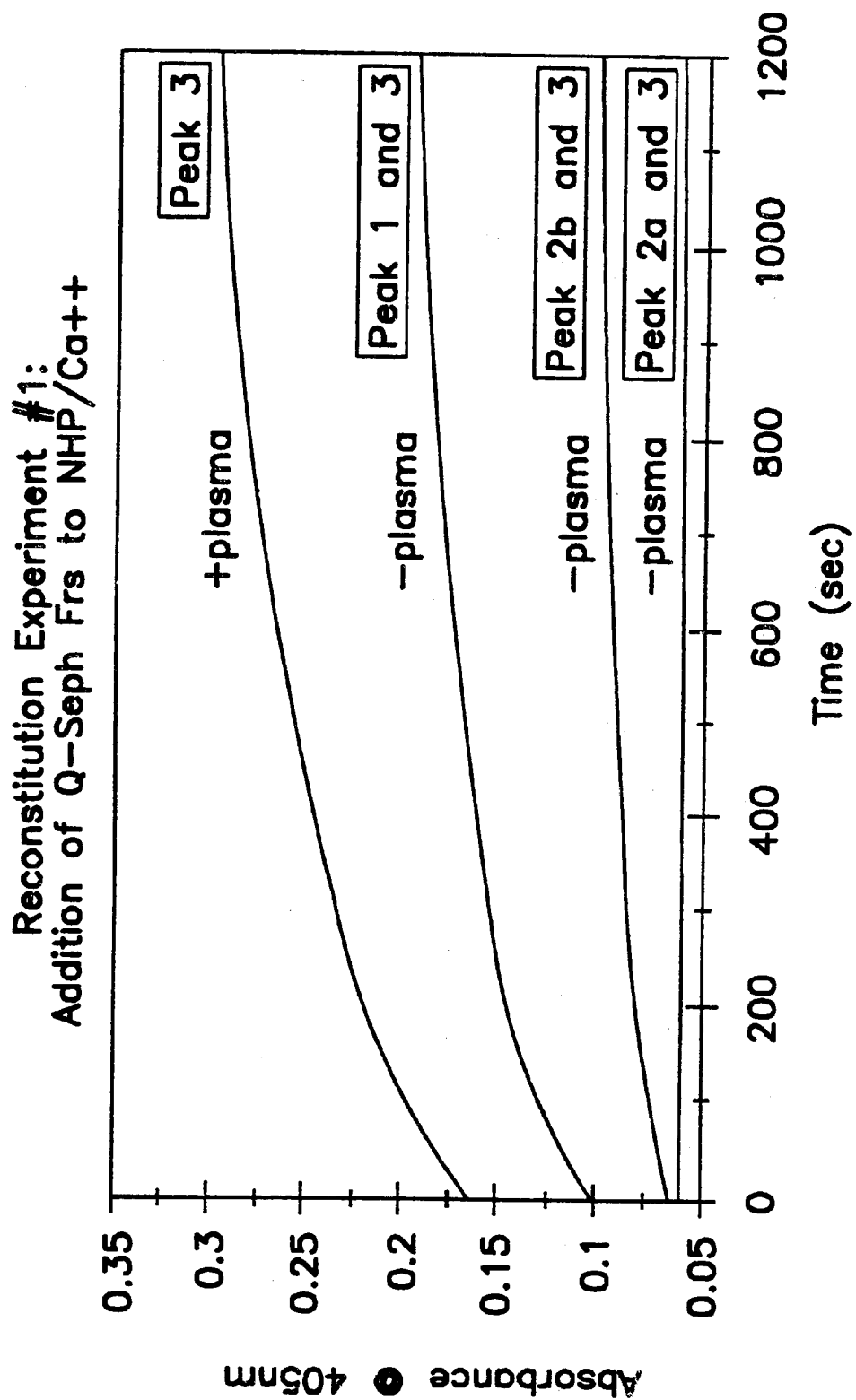
FIG. 23 illustrates the turbidity change upon adding divalent calcium to materials obtained upon Q-sepharose chromatography in the absence of plasma (except top curve)
Figure 25A:
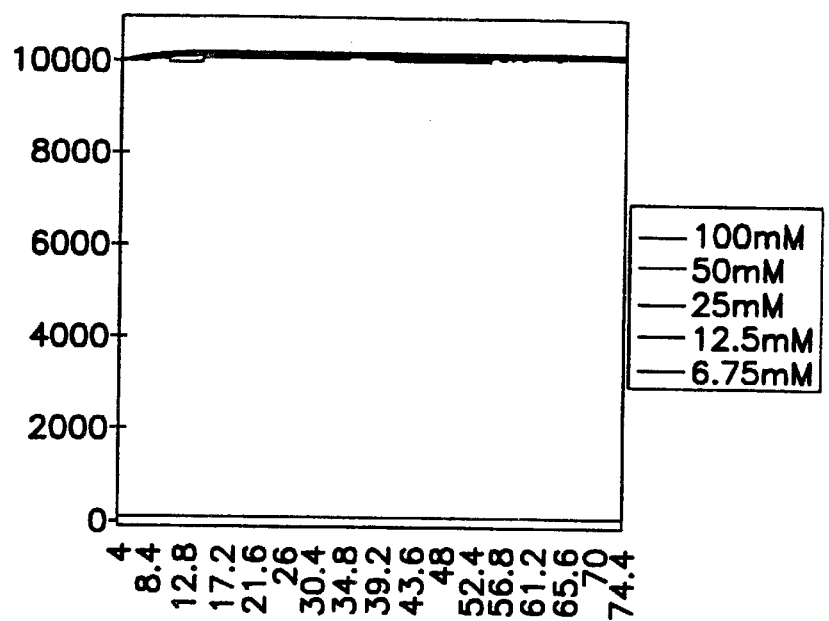
FIG. 25 shows the response to increasing calcium concentrations in optical transmission profiles.
Figure 25B:
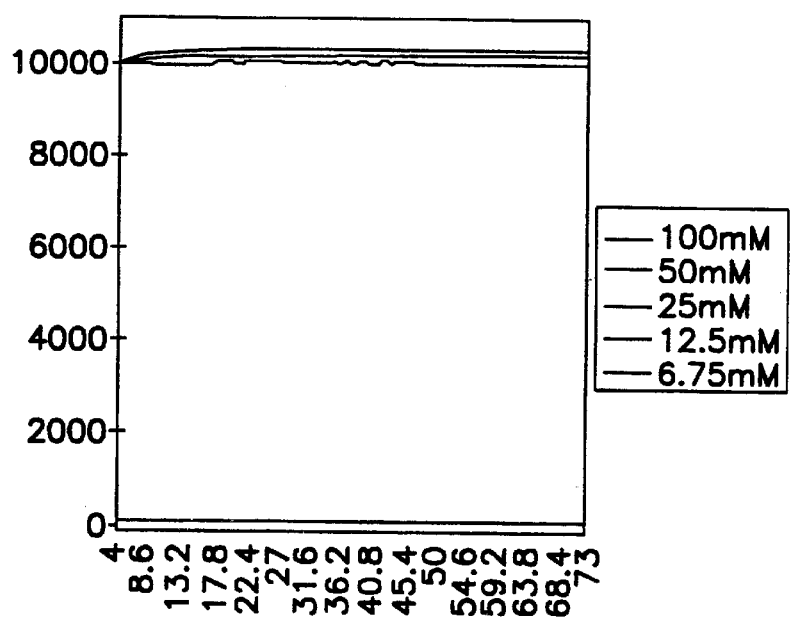
Figure 25C:
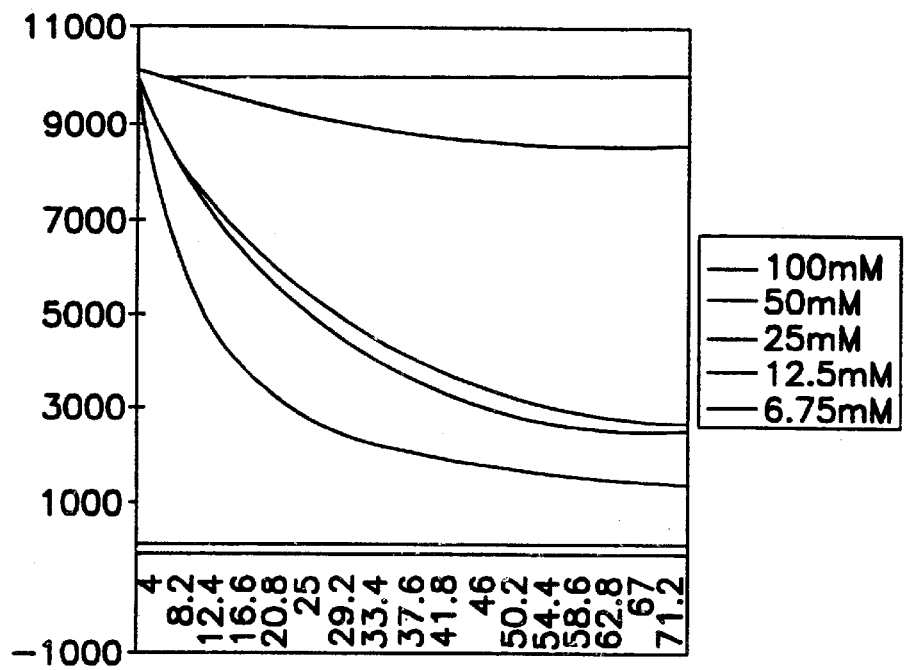
Figure 25D:
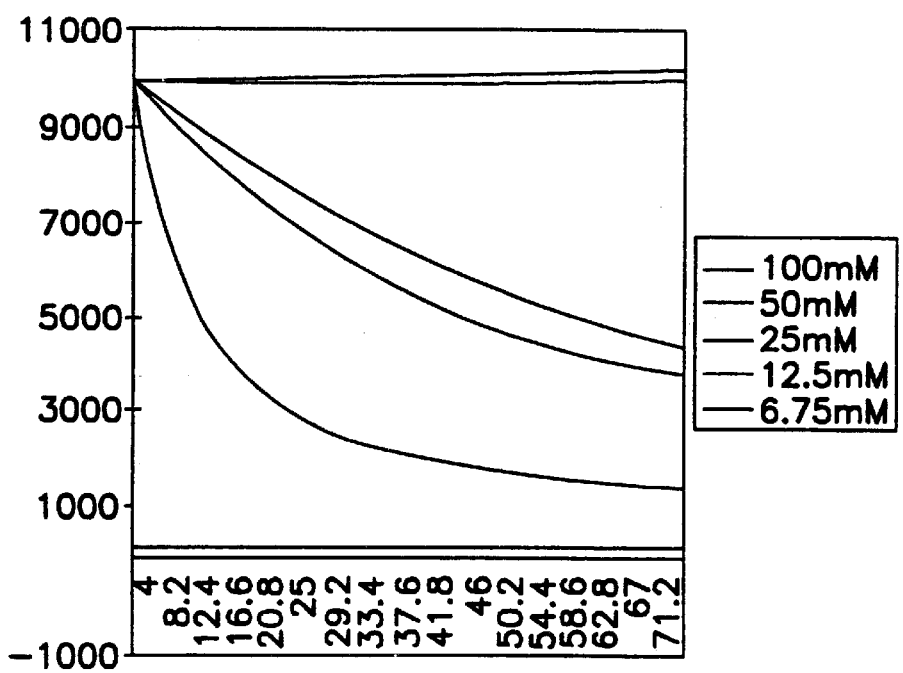

FIG. 23 illustrates the turbidity changes upon adding divalent calcium to materials obtained upon Q-sepharose chromatography in the absence of plasma. No single peak gave a positive response, but a mixture of peak 1 and peak 3 materials did give a positive response indicating the involvement of CRP, a 300 kD protein, and one or more other proteins in the precipitate (peak 3+plasma was the control). FIG. 24 is a table showing CRP, µg/ml determined b ELISA. Delta A405 nm is the maximum turbidity change observed when patients' plasma was recalcified on the presence of the thrombin inhibitor PPACK). FIG. 24, therefore, shows that patients with increased absorbance have varying elevated levels of CRP, once again indicating that more than one protein is involved in the precipitate formation.

In one embodiment of the invention, the reagent to plasma ratio is varied between multiple tests using a reagent that induces precipitate formation. This variance allows for amplifying the detection of the precipitate formation by optimization of reagent to plasma ratio (e.g. varying plasma or reagent concentrations) In the alternative, the slope due to the precipitate formation can be averaged between the multiple tests. As can be seen in FIG. 25, the response to increasing calcium concentrations is shown in optical transmission waveform profiles. The left panels show two normal patients where calcium concentrations were varied (no clotting agents used), whereas the right panels show two patients with haemostatic dysfunction (DIC in these two cases) where the metal cation (calcium) concentration was varied (the calcium alone being incapable of any substantial fibrin polymerization).

Figure 26A:
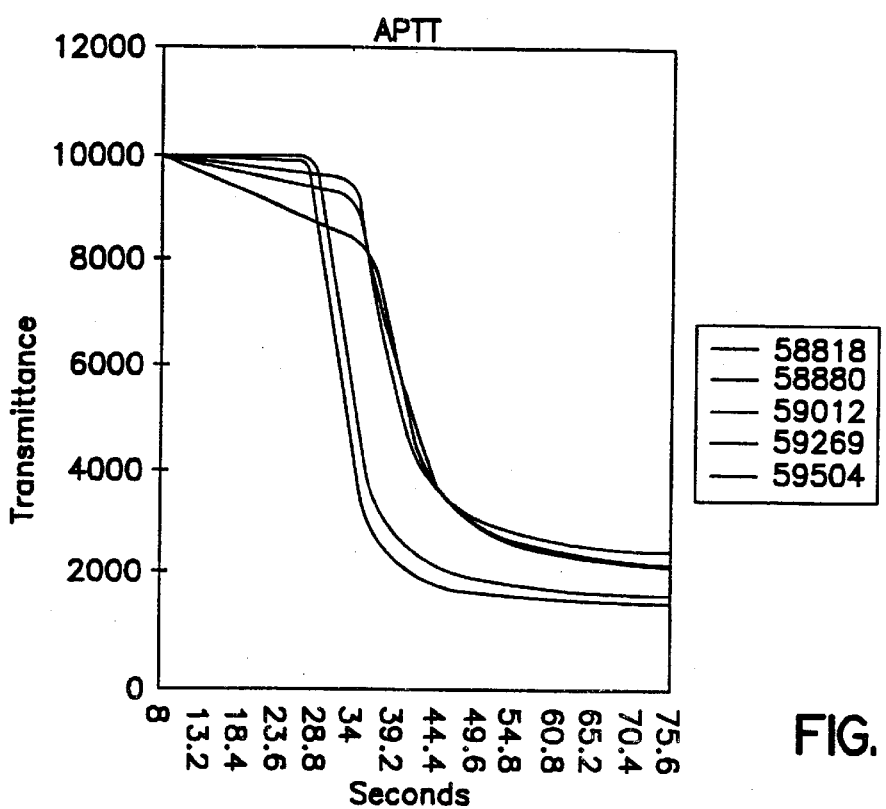
FIG. 26 shows a more pronounced slope without the use of a clotting agent.
Figure 26B:
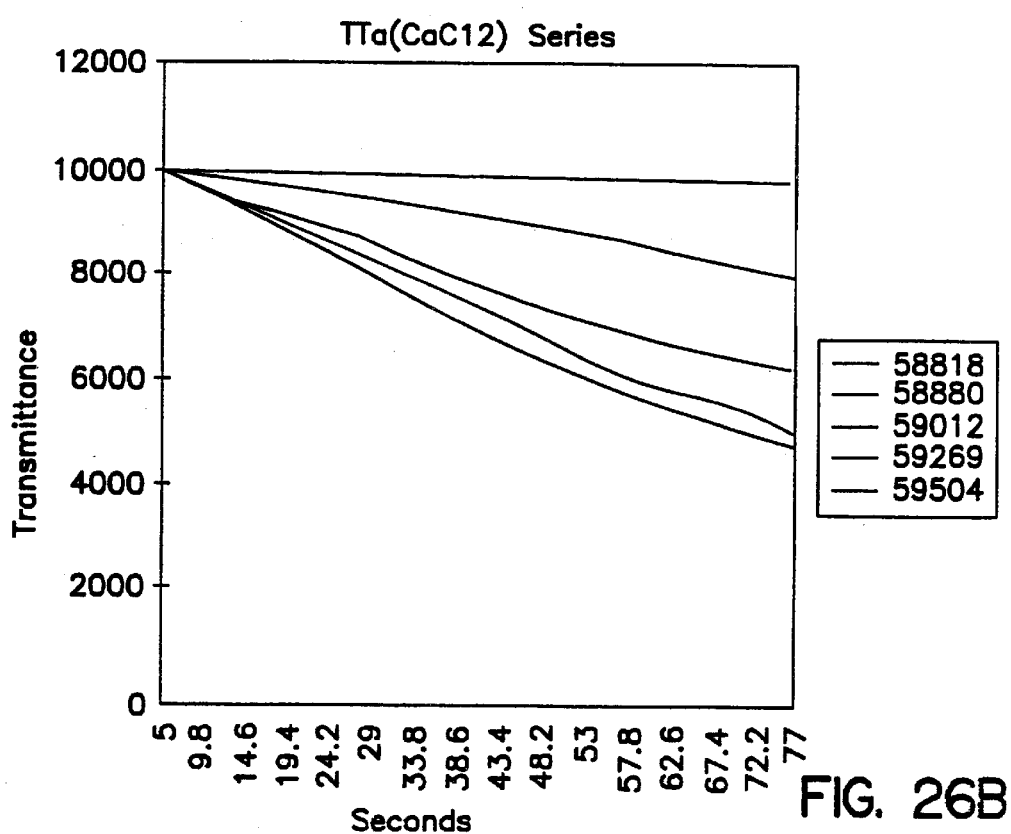
Figure 27:
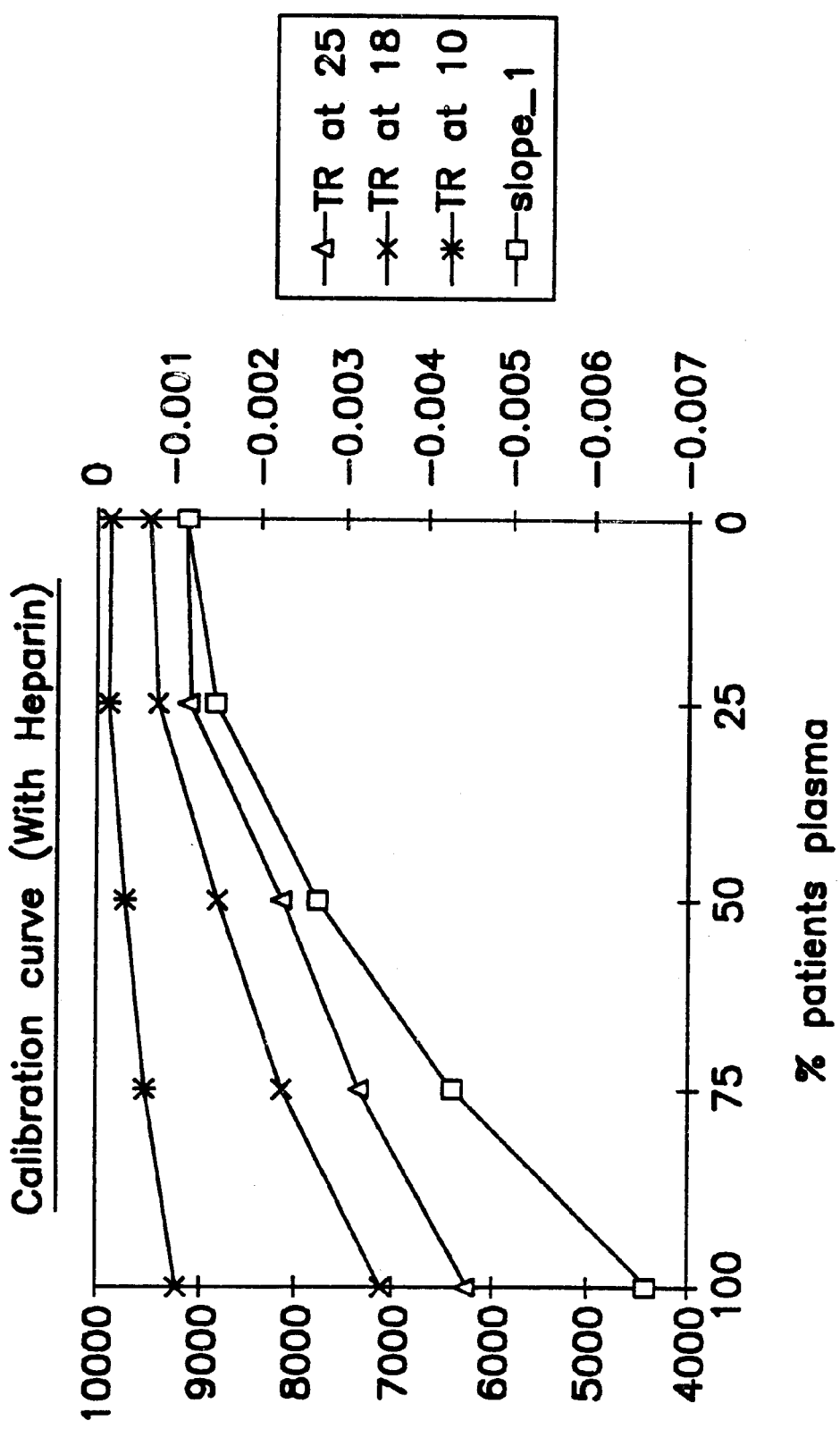
FIG. 27 is a calibration curve with heparin.

Though precipitate formation is capable of being detected an patients with haemostatic dysfunction when a clotting agent is used, it is beneficial that the reagent used is capable of forming the precipitate without fibrin polymerization. As can be seen in FIG. 26, the slope is more pronounced and more easily detectable when a reagent such as calcium chloride is used (right panel) as compared to when a clotting reagent such as an APTT reagent (left panel) is used. As can be seen in FIG. 27, when a clot inhibitor was added (in this case heparin), all parameters including slope_1 gave good results, and slope_1 showed the best sensitivity. For the above reasons, a reagent capable of precipitate formation in the absence of fibrin polymerization and/or a clot inhibitor are preferred.

Figure 28:
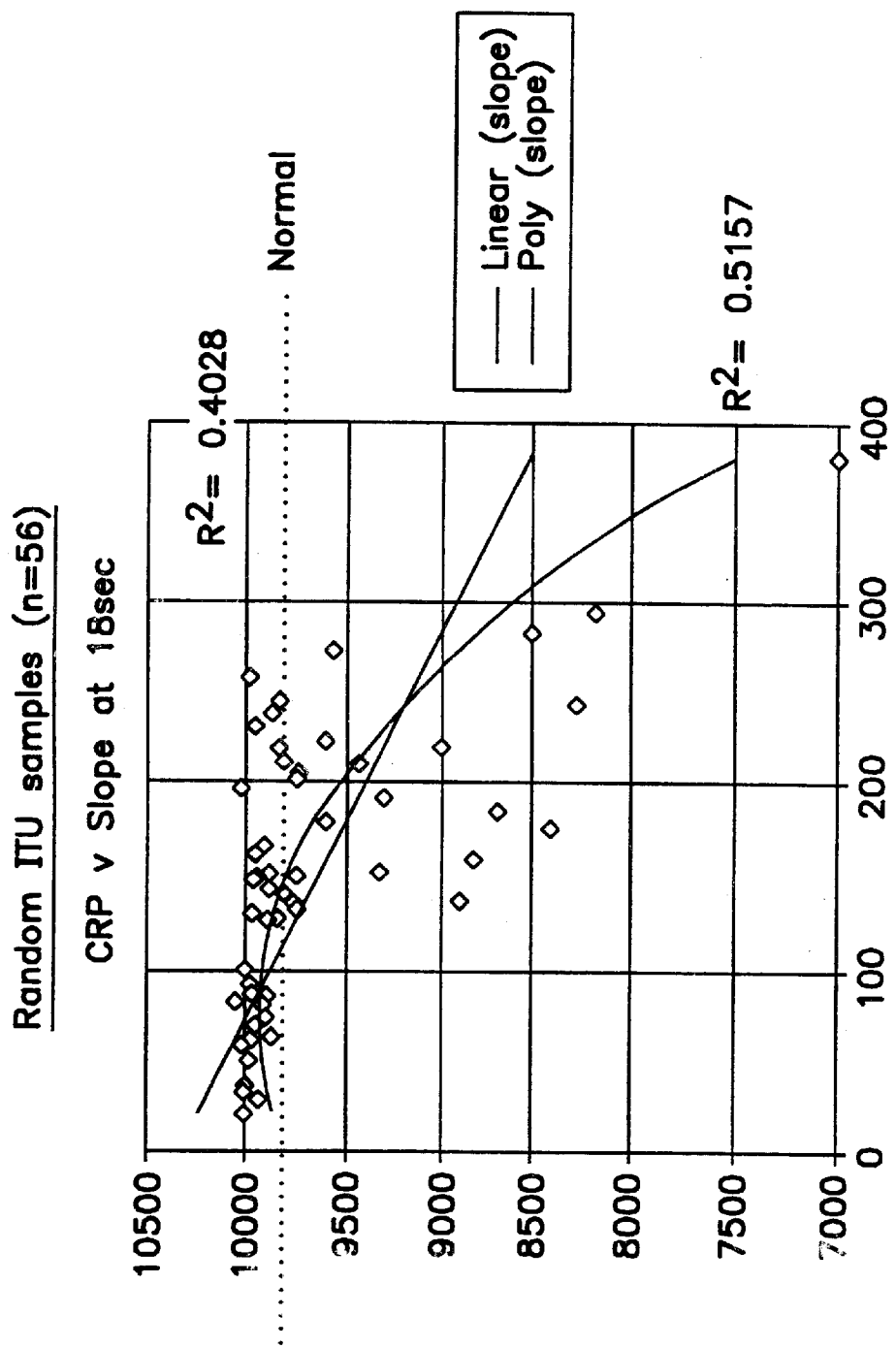
FIG. 28 shows CRP levels in 56 ITU patients plotted against 20 transmittance at 18 seconds.
Figure 29:
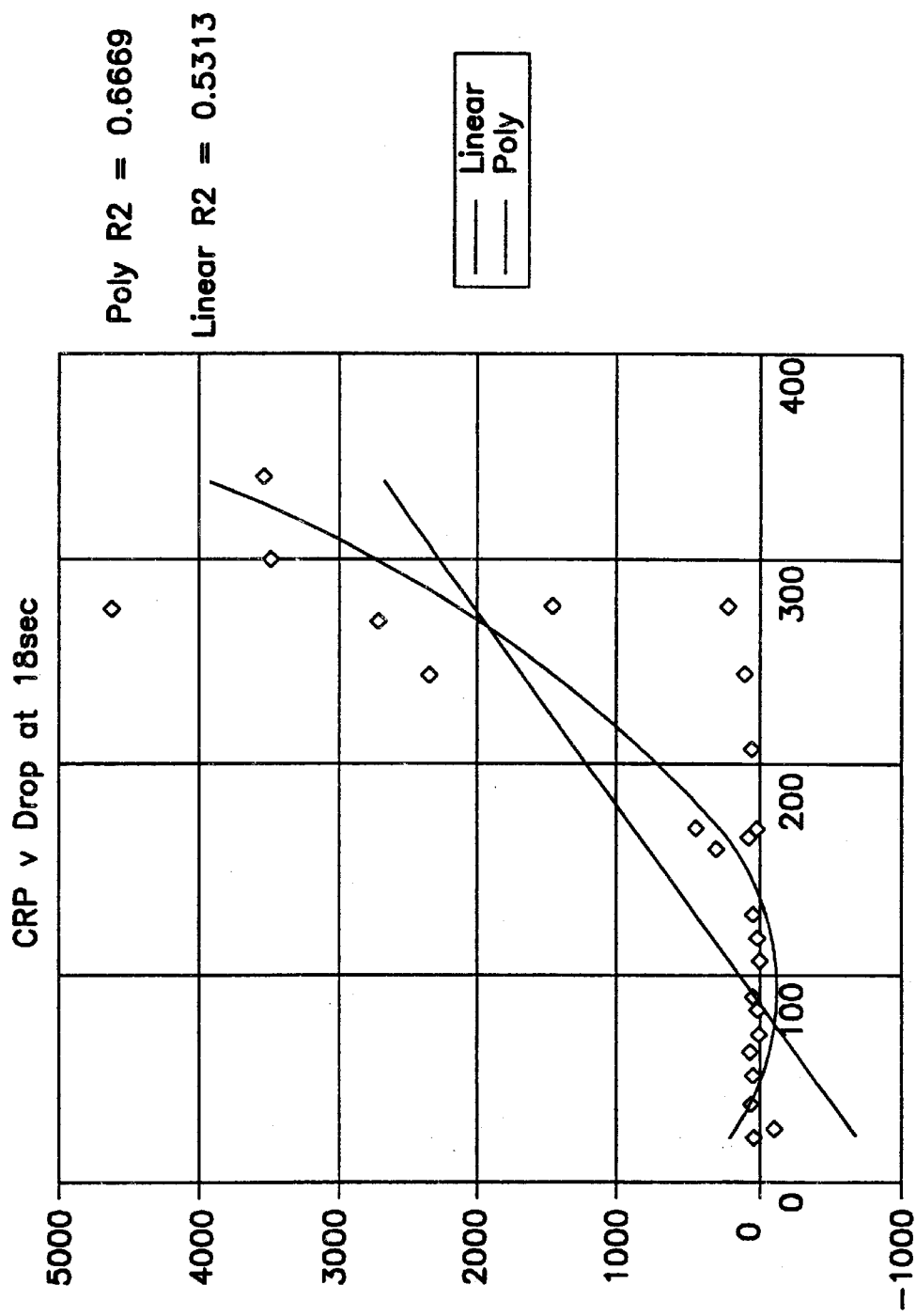
FIG. 29 shows more samples with CRP and decrease in transmittance at 18 seconds (10000—TR18).

As can be seen in FIG. 28, CRP levels from 56 ITU patient were plotted against transmittance at 18 seconds. The dotted line is the cut-off for an abnormal transmittance at 18 seconds. FIG. 29 shows more samples with CRP and decrease in transmittance at 18 seconds (10000—TR18).

These figures indicate that patients with abnormal transmittance levels due to precipitate formation all have increased levels of CRP. However, not all patients with increased levels of CRP have abnormal transmittance levels thus indicating that more than CRP is involved in the precipitate.

In a further embodiment of the invention, the formation of the precipitate comprising a complex of proteins including CRP is detected and/or quantitated, by the use of a latex agglutination assay. In this method, antibodies are raised against wither the 300 kD protein or CRP. Whether monoclonal or polyclonal antibodies are used, they are bound to suitable latex and reacted with a patient test sample or preferably with the precipitate itself having been separated from the rest of the patient plasma, in accordance with known methods. The amount of agglutination of the latex is proportional to the amount of the CRP complex in the sample.

Alternatively, immunoassays can be performed, such as ELISA's, according to known methods (sandwich, competition or other ELISA) in which the existence and/or amount of the complex of proteins is determined. For example, an antibody bound to solid phase binds to CRP in the CRP protein complex. Then, a second labeled antibody is added which also binds to CRP in the CrF protein complex, thus detecting the complex of proteins. In the alternative, the second labeled antibody can be specific for the 300 kD protein in the complex. Or, in a different assay, the antibody bound to solid phase can bind to the 300 kD protein in the complex, with the second (labeled) antibody binding either to the 300 kD protein or to CRP. Such immunoassays could likewise be adapted to be specific for SAA, where antibodies, bound ants labeled, bind to SAA, or where one antibody binds to SAA and the other either to CRP or the 300 kD protein. The above techniques are well known to those of ordinary skill in the art and are outlined in *Antibodies, A Laboratory Manual*, Harlow, Ed and Lane, David, Cold Spring Harbor Laboratory, 1988, the subject matter of which is incorporated herein by reference.

It is to be understood that the invention described and illustrated herein is to be taken as a preferred example of the same, and that various changes in the methods of the invention may be resorted to, without departing from the spirit of the invention or scope of the claims.

We claim:

1. A method comprising:
   a) adding a reagent to a test sample, wherein the test sample comprises at least a component of a blood sample from a patient;
   b) measuring the formation of a precipitate due to the reaction of the test sample and the reagent, over time so as to derive a time-dependent measurement profile, said reagent forming a precipitate in the test sample without causing substantial fibrin polymerization; and
   wherein a clot inhibitor is provided as part of said reagent or as part of an additional reagent added to said test sample.

2. The method according to claim 1, wherein said clot inhibitor comprises one or more of hirudin, heparin, PPACK, I2581, and antithrombin.

3. A method comprising:
   a) adding a reagent to a test sample, wherein the test sample comprises at least a component of a blood sample from a patient;
   b) measuring the formation of a precipitate due to the reaction of the test sample and the reagent, over time so as to derive a time-dependent measurement profile, said reagent forming a precipitate in the test sample without causing substantial fibrin polymerization; and wherein the formation of said precipitate is correlated to the existence of haemostatic dysfunction in the patient.

4. The method according to claim 3, wherein the greater the formation of said precipitate, the worse the existence of haemostatic dysfunction in the patient which can be quantified by constructing a reference curve to compare said patient test sample with previous patient samples.

5. A method comprising:
   a) adding a reagent to a test sample, wherein the test sample comprises at least a component of a blood sample from a patient;
   b) measuring the formation of a precipitate due to the reaction of the test sample and the reagent, over time so as to derive a time-dependent measurement profile, said reagent forming a precipitate in the test sample without causing substantial fibrin polymerization; and
   wherein said method is a method of measuring haemostatic dysfunction in a patient, wherein the time dependent measurement profile is an optical transmission profile, and wherein the greater the decrease in transmission in the test sample, the greater the formation of said precipitate, and the greater the haemostatic dysfunction in the patient.

6. The method according to claim 5, wherein the amount of fibrin polymerization in the method, if any, causes no change in optical transmittance.

7. A method comprising:
   a) adding a reagent to a test sample, wherein the test sample comprises at least a component of a blood sample from a patient;
   b) measuring the formation of a precipitate due to the reaction of the test sample and the reagent, over time so as to derive a time-dependent measurement profile, said reagent forming a precipitate in the test sample without causing substantial fibrin polymerization; and
   wherein said precipitate comprises a protein weighing approximately 20 kD.

8. The method according to claim 7, wherein said protein is insoluble in saline, EDTA and Imidazole, and soluble in 5 molar urea.

9. A method for determining whether or not a patient has haemostatic dysfunction, comprising:
   a) obtaining a blood sample from a patient;
   b) obtaining plasma from said blood sample;
   c) adding to said plasma a reagent capable of inducing the formation of a precipitate in patients with haemostatic dysfunction without causing any substantial fibrin polymerization;
   d) taking one or more measurements of a parameter of the sample wherein changes in the sample parameter are capable of correlation to precipitate formation if present; and
   e) determining that a patient has haemostatic dysfunction if precipitate formation is detected.

10. The method according to claim 9, wherein a plurality of measurements are made after addition of said reagent.

11. The method according to claim 9, wherein a single reagent is used prior to taking said measurements.

12. The method according to claim 9, wherein said measurements are measurements of optical transmission or absorbance through said sample.

13. The method according to claim 12, wherein said reagent comprises a metal ion.

14. The method according to claim 13, wherein said metal ion comprises one or more of calcium, magnesium, manganese, iron or barium.

15. The method according to claim 9, wherein a clot inhibitor is provided as part of said reagent or as part of an additional reagent added to said sample.

16. The method according to claim 15, wherein said clot inhibitor comprises one or more of hirudin, heparin, PPACK, I2581 or antithrombin.

17. The method according to claim 9, wherein said one or more measurements are unaffected by clot formation due to lack of fibrin polymerization.

18. The method according to claim 9, wherein the one or more measurements are a plurality of measurements, and wherein a rate of change of said plurality of measurements is determined, and wherein haemostatic dysfunction is determined based on the determined rare of change.

19. The method according to claim 9, wherein said haemostatic dysfunction is disseminated intravascular coagulation.

20. A method comprising:
   a) adding a coagulation reagent to a first aliquot of a test sample from a patient, wherein said test sample is a sample of whole blood or a portion thereof;
   b) monitoring the formation of fibrin over time in said test sample by measuring a parameter of said test sample which changes over time due to addition of said coagulation reagent;
   c) determining a rate of change, if any, of said parameter in a period of time prior to formation of fibrin in said test sample;
   d) if said determined rate of change is beyond a predetermined threshold, then with a second aliquot of said patient test sample, adding thereto a reagent that induces the formation of a precipitate in the absence of fibrin polymerization;
   e) measuring the formation of the precipitate over time; and
   f) determining the possibility or probability of haemostatic dysfunction based on the measurement of the precipitate.

21. The method according to claim 20, wherein said coagulation reagent is a PT reagent or an APTT reagent.

22. The method according to claim 21, wherein said reagent that causes precipitate formation is a divalent metal cation.

23. The method according to claim 22, wherein said divalent metal cation is calcium, magnesium, manganese, iron or barium.

24. The method according to claim 22, wherein said reagent that causes precipitate formation comprises a clot inhibitor.

25. The method according to claim 24, wherein said clot inhibitor is hirudin, heparin, PPACK, I2581 or antithrombin.

26. The method according to claim 20, further comprising the step of determining a clotting time for said first aliquot, and wherein at least one measurement in the test of the second aliquot with the reagent capable of forming a precipitate without causing fibrin polymerization is at a time greater than the clotting time of the first aliquot.

27. A method comprising:
   a) adding a reagent to a patient sample, said sample including at least a component of blood, the reagent being capable of causing formation of a precipitate in said sample without causing substantial fibrin polymerization;

b) monitoring a changing parameter of said sample over time, said parameter indicative of said precipitate formation;

c) determining the rate of change of said parameter or whether said parameter exceeds a predetermined limit at a predetermined time;

d) repeating steps a) to c) at least once, each time at a different sample/reagent ratio;

e) measuring at least one of the maximum, average or standard deviation for the measurements in step c); and f) determining haemostatic dysfunction based on the at least one measurement of step e).

28. The method according to claim 27, further comprising repeating steps a) to e) at a later time or date to monitor disease progression or regression.

29. The method according to claim 27, wherein said haemostatic dysfunction is disseminated intravascular dysfunction or haemostatic dysfunction with the potential to lead to disseminated intravascular coagulation.

30. The method according to claim 27, wherein said reagent further comprises a clot inhibitor.

31. The method according to claim 30, wherein said reagent comprises a metal cation capable of inducing precipitate formation.

32. The method according to claim 31, wherein said reagent comprises calcium, magnesium, manganese, iron or barium as divalent cations.

33. The method according to claim 27, wherein said different sample/reagent ratios are a result of altering the concentration of said reagent from test to test.

34. The method according to claim 28, wherein said different sample/reagent ratios are a result of altering the concentration of said patient sample from test to test.

35. The method according to claim 34, wherein said patient sample is a plasma sample that is diluted at different ratios from test to test.

* * * * *